US007829578B1

(12) United States Patent
Riscoe et al.

(10) Patent No.: US 7,829,578 B1
(45) Date of Patent: Nov. 9, 2010

(54) AROMATIC KETONES AND USES THEREOF

(75) Inventors: Michael K. Riscoe, Tualatin, OR (US); Rolf W. Winter, Portland, OR (US); Jane X. Kelly, Lake Oswego, OR (US); Martin J. Smilkstein, Portland, OR (US); David J. Hinrichs, Lake Oswego, OR (US)

(73) Assignees: Oregon Health & Science University, Portland, OR (US); U.S. Department of Veterans Affairs, Washington, DC (US)

( * ) Notice: Subject to any disclaimer, the term of this patent is extended or adjusted under 35 U.S.C. 154(b) by 900 days.

(21) Appl. No.: 11/633,509

(22) Filed: Dec. 5, 2006

Related U.S. Application Data

(60) Provisional application No. 60/749,084, filed on Dec. 12, 2005.

(51) Int. Cl.
  *C07D 215/38* (2006.01)
  *A61K 31/04* (2006.01)
(52) U.S. Cl. .................. 514/312; 546/153; 546/159
(58) Field of Classification Search ................. 546/153, 546/159; 514/312
  See application file for complete search history.

(56) References Cited

U.S. PATENT DOCUMENTS

| | | | |
|---|---|---|---|
| 2,647,901 | A | 8/1953 | Archer |
| 2,709,171 | A | 5/1955 | Stoughton |
| 2,732,373 | A | 1/1956 | Steiger |
| 2,732,374 | A | 1/1956 | Steiger |
| 3,981,903 | A | 9/1976 | Hirano et al. |
| 4,250,182 | A | 2/1981 | Gorvin |
| 5,977,077 | A | 11/1999 | Winter et al. |
| 6,248,891 | B1 | 6/2001 | Sharp et al. |
| 6,541,483 | B2 | 4/2003 | Michejda et al. |
| 6,613,797 | B2 | 9/2003 | Winter et al. |
| 6,686,469 | B2 | 2/2004 | Eberle et al. |
| 6,703,388 | B2 | 3/2004 | Miyamoto et al. |
| 2002/0055644 | A1 | 5/2002 | Winter et al. |

FOREIGN PATENT DOCUMENTS

| | | |
|---|---|---|
| DE | 551 029 | 5/1932 |
| EP | 0 110 298 | 6/1984 |
| WO | WO 2008/064011 A1 | 5/2008 |

OTHER PUBLICATIONS

Ambroise-Thomas, P. "Antimalarial vaccines. Disappointments and hopes." *Bull Acad. Natl. Med.*, (1997), 181: 1637-50.
Atkinson, et al., "Ultrastructure of Malaria-Infected Rrythrocytes," *Blood Cells.* (1990) 16: 351-368.
Bojang, et al., "Follow-up of Gambian Children Recruited to a Pilot Safety and Immunogenicity Study of the Malaria Vacinne SPf66," *Parasite Immunology*, (1997): 19: 579-81.
Boudreau, et al., "Tolerability of Prophylactic Lariam® Regimens," *Trop. Med. Parasitol*, 44, (1993): 257-265.
Brewer, et al., "Factors Relating to Neurotoxicity of Artemisinin Antimalarial Drugs Listening to Arteethe," *Med. Trop.*, (*Mars*) (1998), 58: 22-7.
Brewer, et al., "Neurotoxicity in Animals Due to Arteether and Artemether," *Transactions of the Royal Society of Tropical Medicine and Hygiene*, (1994), 88 (Supp. 1); S33-6.
Broudy, et al., "Monocytes Stimulate Fibroblastoid Bone Marrow Stromal Cells to Produce Multilineage Hematopoietic Growth Factors," *Blood*, (1986) vol. 68, No. 2, 530-534.
Clark, et al., "Developmental Toxicity of Artesunate and an Artesunate Combination in the Rat and Rabbit," (2004), *Birth Defects Research (Part B)*, 71: 380-394.
Coleman, et al., "Gametocytocidal and Sporontocidal Activity of Antmalarials Against *Plasmodium berghei anka* in ICR Mice and *Anopheles stephensi* Mosquitoes," (1992), *Am. J. Trop. Med. Hyg.* 46: 169-82.
Croft, et al., "The Activity of Hydroxynaphthoquinones Against *Leishmania donovani*," (1992), *Journal of Antimicrobial Chemotherapy* 30: 827-832.
Doolan, et al., "DNA Vaccination as an Approach to Malaria Control: Current Status and Stragegies," (1998), *Curr. Top Microbiol. Immunol.*, 226: 37-56.
Fivelman, et al., "Modified Fixed-Ratio Isobologram Method for Studying in Vitro Interactions between Atovaquone and Progunanil or Dihydroartemisinin Against Drug-Resistant Strains of *Plasmodium falciparum*," (2004), *Antimicrob. Agents Chemother.*, 48: 4097-102.

(Continued)

*Primary Examiner*—D. Margaret Seaman
(74) *Attorney, Agent, or Firm*—Klarquist Sparkman, LLP

(57) ABSTRACT

Aromatic ketones having an extended fluoro-alkyl or fluoro-alkoxy moiety are disclosed. In particular aspects, the compounds comprise substituted 9-acridone, 9-xanthone, 4(1H)-quinolone, 4(1H) pyridone, 1,4-naphthoquinone, 9,10-anthraquinone derivatives. These preparations possess potent pharmacological activity for inhibiting malaria and mosquito-borne (*Plasmodium*) diseases. The haloalkyl/alkoxy aromatic compounds possess significant pharmacological activity, with $IC_{50}$ values in the nanomolar and sub-nanomolar range, and reduced toxicity against host derived cells and tissues. Methods of using the fluoro-alkyl/alkoxy aromatic compounds in the treatment of malaria and other human and animal diseases are also disclosed. Agricultural uses of the fluoro-alkyl/alkoxy aromatic compounds, such as in control of fungal diseases and in the production of important commercial crops (apples, etc.), are also presented.

19 Claims, 4 Drawing Sheets

OTHER PUBLICATIONS

Fusetti, et al., "Meflochina ed ototossicità: descrizione di tre casi," (1999) *Clin. Ter.* 150: 379-382.

Guillouzo, André, "Liver Cell Models in in Vitro Toxicology," (1998), *Environ. Health Perspect.*, 106: (Suppl 2): 511-32.

Hudson, A., "Atovaquone-A Novel Broad-Spectrum Anti-Infective Drug," (1993), *Parasitol Today*, 9: 66-8.

Hudson, A., "566C80: A Potent Broad Spectrum Anti-Infective Agent with Activity Against Malaria and Opportunistic Infections in AIDS Patients," (1991), *Drugs Exptl. Clin. Res.* XV11(9) 427-435.

Ignatushchenko, et al., "Xanthones as Antimalarial Agents; Studies of a Possible Mode of Action," (1997), *FEBS, Lett.*, 409: 67-73. X.

Ignatushchenko, et al., "Xanthones as Antimalarial Agents: Stage Secificity," (2000) *Am. J. Trop. Med. Hyg.*, 62: 77-81.

Kelly, et al., "A Spectroscopic Investigation of the Binding Interactions Between 4,5-dihydroxyxanthone and heme," *Journal of Inorganic Biochemistry* 86 (2001) 617-625.

Kelly, et al. "Optimization of Xanthones for Antimalarial Activity: the 3,6-Bis-w-Diethylaminoalkoxyxanthone Series," *Antimicrobial Agents and Chemotherapy*, 2002, 46: 144-50.

Kelly, et al., "The Kinetics of Uptake and Accumulation of 3,6—bis-ω-diethylamino-amyloxyxanthone by the Human Malaria Parasite *Plasmodium falciparum*," (2002), *Molecular & Biochemical Parasitology*, 123: 47-54.

Kessl, et al., "Cytochrome *b* Mutations That Modify the Ubiquinol-binding Pocket of the Cytochrome $bc_1$ Complex and Confer Antimalarial Drug Resistance in *Saccharomyces cerevisiae*," *The Journal of Biological Chemistry*, (2005), vol. 280, No. 17, Apr. 28, pp. 17142-17148.

Kessl, et al., "Molecular Basisfor Atovaquone Resistance in *Pneumocystis jirovecii* Modeled in the Cytochrome $bc_1$ Complex of *Saccharomyces cerevisiae*," *The Journal of Biological Chemistry*, (2004), vol. 279, No. 4, Jan. 23, pp. 2817-2824.

Korsinczky, et al., "Mutations in *Plasmodium falciparum* Cytochrome *b* That Are Associated with Atovaquone Resistance Are Located at a Putative Drug-Binding Site," *Antimicrobial Agents and Chemotherapy*, Aug. 2001, pp. 2100-2108.

Krungkrai, J., "The multiple roles of the mitochondrion of the malarial parasite," *Parasitology*, (2004), 129, 511-524.

Learngaramkul, et al., "Molecular Characterization of Mitochondria in Asexual and Sexual Blood Stages of *Plasmodium falciparum*," *Molecular Cell Biology Research Communications* (1999), 2, 15-20.

Li, et al., "Cryopreserved human hepatocytes: characterization of drug-metabolizing enzyme activities and applications in Higher Throughput Screening Assays for Hapatoxicity, Melabolic Stability, and Drug-Drug Interaction Potential," *Chemical-Biological Interaction* (1999), 121, 17-35.

Low, L. K. "Metabolic Changes of Drugs and Related Organic Compounds," Chapter 3, pp. 43-12 in J. N. Delgado and W.A. Remers (ed.), *Wilson and Gisvold's Textbook of Organic Medicinal and Pharmaceutical Chemistry, 10th edition*, (1998) Raven Publishers, Philadelphia.

Luzzi, et al., "Adverse Effects of Antimalarials—An Update," *Drug Safety* (1993) 8 (4); 295-311.

Madan, et al., "Effect of Cryopreservation onCytochrome P-450 Enzyme Induction in Cultured Rat Hepatocytes," *Drug Metabolism and Disposition*, (1999), *Drug Metabolism and Disposition* (1999), 27: 327-35.

Makler, et al., "Detection of *Plasmodium falciparum* Infection with the Fluorescent Dye, Benzothiocarboxypurine," *Am.J. Trop. Med. Hyg.*, (1991), 44(1), pp. 11-16 (90-191).

Meshnick, Steven R., "Multiple Cytochrome b Mutation May Cause Atovaquone Resistance," *The Journal of Infectious Diseases*, (2005), 44: 11-6.

Milhous, W. K., "Development of New Drugs for Chemoprophylaxis of Malaria," *Med. Trop.* (2001), 61: 48-50.

Olliaro, et al., "An Overview of Chemotherapeutic Targets for Antimalarial Drug Discovery," *Pharmacol Ther.*, (1999), 81: 91-110.

Pessina, et al., "Application of the CFU-GM Assay to Predict Acute Drug-Induced Neutropenia: AnInternational Blind Trial to Validate a Prediction Model for the Maximum Tolerated Dose (MTD) of Myelosuppressive Xenobiotics," *Toxicological Sciences*, (2003) 75, 367.

Pessina, et al., "In Vitro Tests for Haematotoxicity: Prediction of Drug-Induced Myelosupresson by the CFU-GM Assay," *ATLA* 30, (2002), Supplement 2, 75-79.

Raether, W., "Antimalarial Activity of Floxacrine (HOE 991) Studies on blood schizontocidal action of Floxacrine against *Plasmodium berghei, P. vinckei* and *P. cynomolgi*," *Annals of Tropical Medicine and Parasitology*, (1979), vol. 73, No. 6.

Rathbun, R. Kearney, "Interferon-γ-Induced Apoptotic Responses of Fanconi Anemia Group C Hematopoietic Progenitor Cells Involve Caspase 8-Dependent Activatinof Caspase 3 Family Members," *Blood*, Dec. 15, 2000, vol. 96, No. 13.

Schmidt, L. H., "Antimalarial Properties of Floxacrine, a Dihydroracridinedione Derivative," *Antimicrobial Agents and Chemotherapy*, Oct. 1979, vol. 16, No. 4, pp. 475-485.

Slomianny, et al., "A Cytochemical Ultrastructural Study of the Lysosomal System of Different Species of Malaria Parasites," *J. Protozool*, (1990), 37: 465-70.

Smilkstein, et al., "Simple and Inexpensive Fluorescence-Based Technique for High-Throughput Antimalarial Drug Screening," *Antimicrobial Agents and Chemotherapy* May 2004, pp. 1803-1806.

Srivastava, et al., "Resistance Mutations Reveal the Atovaquone-Binding Domain of Cytochrome *b* in malaria parasites," *Molecular Microbiology* (1999) 33(4), 704-711.

Srivastava, et al., "Atovaquone, a Broad Spectrum Antiparasitic Drug, Collapses Mitochondrial Membrane Potential ina Malarial Parasite," *The Journal of Biological Chemistry* Feb. 14, 1997, vol. 272, No. 7, pp. 3961-3967.

Suswam, et al., "*Plasmodium falciparum*: The Effects of Atovaquone Resistance on Respiration," *Experimental Parasitology* (2001), 98, 180-187.

Taylor, et al., "Antimalarial Drug Toxicity" *Drug Safety*, (2004), 27 (1) : 25-61.

Toovey, et al., "Audiometric changes associated with the treatment of uncomplicated *falciparum* malaria with co-artemether," *Transactions of the Royal Society of Tropical Medicine and Hygiene* (2004) 98, 261-267.

Trouiller, et al., "Drug Development Output from 1975 to 1996: What Proportion for Tropical Diseases?" *Int. J. Infect. Dis.* (1998), 3: 61-3.

Trouiller, et al., "Drug Development Output: what proportion for tropical diseases?" (1999) *Lancet*, 354: 164.

Turker, M.S., "Estimation of mutation frequencies in normal mammalian cells and the development of cancer," *Seminars in Cancer Biology*, (1998), vol. 8, pp. 407-419.

Vaidya, A. "Mitochondrial Physiology as a Target for Atovaquone and Other Antimalarials," I. Sherman (ed.), *Malaria: Parasite Biology, Pathogenesis, and Protection, American Society for Microbiology*, Washington, D.C. (1998) p. 355-368.

Vaidya, et al., "Atovaquone resistance in malaria parasites," *Drug Resistance Updates* (2000), 3: 283-287.

Varney, et al, "Long-Term Neuropsychological Sequelae of Fever Associated With Amnesia," *Archives of Clinical Neuropsychology*, (1994) vol. 9, No. 4, pp. 347-352.

Varney, et al., "Neuropsychiatric Sequelae ofCerebral malaria in VietnamVeterans," *The Journal of Nervous and Mental and Diseases* (1997), 185: 695-703.

Via, et al., "Effects of Cytokines on mycobacterial phagosome maturation," *Journal of Cell Science* (1998), 111: 897-905.

Weina, P.J., "From Atabrine in World War II to Mefloquine in Somalia: The Role of Education in Preventive Medicine," *Military Medicine*, (1998), 163: 9: 635.

Winkelmann, et al., "Antimalarial and Antiococcidial Activity of 3-Aryl-7-chloro-3, 4-dihydroacridine-1,9-(2H,10H)-diones," *Arzneim. Forsch/Drug Res.* (2000), 37 (1) 647-61.

Peters, et al., "The Chemotherapy of Rodent Malaria, XXIII, Casual prohylaxis, part II: Practical experience with *Plasmodium yoelii nigeriensis* in drug screening," *Annals of Tropical Medicine and Parasitology*, (1975), vol. 69, No. 3.

Ager, et al, "Rodent Malaria Models," (1984), 68/I. Springer-Verlag, Berlin.

Adams, et al., "The Iron Environment in Heme and Heme-Antimalarial Complexes of Pharmacological Interest," *Journal of Inorganic Biochemistry*, (1996), 63, 69-77.

Ahua, et al., "Antileishmanial and antifungal acridone derivatives from the roots of *Thamnosma rhodesica*," *Phytochemistry* (2004), 65: 963-8.

Bastow, K. F. "New Acridone Inhibitors of Human Herpes Virus Replication," *Current Drug Targets-Infections Disorders* (2004), 4, 323-330.

Carter, et al., "Evolutionary and Historical Aspects of the Burden of Malaria," *Classical Microbiology Reviews*, Oct. 2002, p. 564-594.

Fujioka, et al., "Activities of New Acridone Alkaloid Derivatives against *Plasmodium yoelii* in vitro," *Arzneim-Forsch/Drug Res.* (1990). 40 (11), Nr. 9.

Michael, J. P., "Quinoline, quinazoline and acridone alkaloids," *Nat. Prod. Rep.*, (2001), 18, 543-559.

Michael, J. P., "Quinoline, quinazoline and acridone alkaloids," *Nat. Prod. Rep.*, (2003), 20, 476-493.

Phillips-Howard, et al., "CNS Adverse Events Associated With Antimalarial Agents," *Drug Safety* (1995) 12 (6): 370-383.

Sachs, et al., "The economic and social burden of malaria," *Nature*, Feb. 2002, vol. 415.

White, Nicholas J., "Antimalarial drug resistance," *The Journal of Clinical Investigation*, Apr. 2004, vol. 113, No. 8.

White, et al., "Averting a malaria disaster," *The Lancet*, Jun. 5, 1999, vol. 353.

Oettmeier, et al., "Inhibition of electron transport through the $Q_p$ Site in Cytochrome $b$ / $c_1$ complexes by acridones," *Biochimica et Biophysica Acta 1188* (1994) 125-130.

Gogal, Jr., et al., "A new rapid and simple non-radioactive assay to monitor and determine the proliferation of lymphocytes: an alternative to [$^3$H]thymidine incorporation assay," *Journal of Immunological Methods* 170 (1994) 211-224.

Fidock, et al., "Antimalarial Drug Discovery: Efficacy Models for Compound Screening," *Nature Reviews/Drug Discovery*, Jun. 2004, vol. 3, 509-20.

Lowden, et al, "Cell culture replication of herpes simplex virus and, or human cytomegalovirus is inhibited by 3,7-dialkoxylated, 1-hydroxyacridone derivatives," available online at www.sciencedirect.com, Activiral Research 59 (2003) 143-154.

Anderson et al., "Parallel synthesis of 9-aminoacridines and their evaluation against chloroquine-resistant *Plasmodium falciparum*," *Bioorganic & Medicinal Chemistry* 14(2):334-343, Jan. 15, 2006.

Kelly et al., "Orally Active Acridones as Novel and Potent Antimalarial Chemotypes," Abstract, *ASTMH 55$^{th}$ Annual Meeting*, Atlanta, Georgia, 1 page (Nov. 12-16, 2006).

Kelly et al., "Structure-Activity Relationships of Orally Active Antimalarial Acridones: Synthesis, Optimization, and Biological Activity," Abstract, *ASTMH 55$^{th}$ Annual Meeting*, Atlanta, Georgia, 1 page (Nov. 12-16, 2006).

Riscoe et al., "Evaluation and Lead Optimization of Antimalarial Aromatic Ketones," Abstract, *ASTMH 55$^{th}$ Annual Meeting*, Atlanta, Georgia, 1 page (Nov. 12-16, 2006).

Smilkstein et al., "Novel Antimalarial Acridone Derivatives with Both Intrinsic Potency and Synergy with Selected Quinolines: in Vitro and in Vivo Studies," Abstract, *ASTMH 55$^{th}$ Annual Meeting*, Atlanta, Georgia, 1 page (Nov. 12-16, 2006).

International Search Reported dated Mar. 31, 2008, from International Application No. PCT/US2007/084560.

US 7,829,578 B1

AROMATIC KETONES AND USES THEREOF

RELATED APPLICATIONS

This application claims the benefit of U.S. provisional application No. 60/749,084, filed Dec. 12, 2005, which is hereby incorporated by reference herein.

GOVERNMENT INTEREST STATEMENT

The United States Government may have rights to the invention described herein as research relevant to the development of the invention was funded by United States governmental grant funds from the United States Department of Veterans Affairs Medical Research Program.

STATEMENT OF JOINT RESEARCH AGREEMENT

In compliance with 37 C.F.R. §1.71(g)(1), disclosure is herein made that the claimed invention was made pursuant to a Joint Research Agreement as defined in 35 U.S.C. 103 (c)(3), that was in effect on or before the date the claimed invention was made, and as a result of activities undertaken within the scope of the Joint Research Agreement, by or on the behalf of the Oregon Health & Sciences University and the United States of America, as represented by the United States Department of Veterans Affairs.

BACKGROUND

1. Field of the Invention

The present invention relates generally to the field of pharmacologically active preparations and particularly to pharmacologically active preparations that are useful in the treatment and/or prevention of infectious diseases (especially parasitic diseases such as malaria), as optimized naphthoquinones, acridones, quinolones, pyridones, anthraquinones, xanthones, and derivatives thereof having anti-parasitic activity is disclosed.

2. Related Art

Malaria has plagued mankind since the beginning of civilization and is believed to be responsible for roughly half of all human deaths that have ever occurred. Malaria remains the most significant parasitic disease in the tropics and sub-tropics, where it causes at least 300 million clinical episodes and claims 1.5 million victims each year.

With a worldwide resurgence in the incidence of malaria, the spread of multi-drug-resistant strains of *Plasmodium falciparum*, the emergence of chloroquine-resistant *P. vivax*, and the increasing resistance of *Anopheline* mosquitoes to insecticides, malaria remains an enormous threat to the millions of people who travel to the tropics and subtropics each year[3].

Malaria is a worsening global health problem. The incidence of malaria continues to increase worldwide, due in part to the emergence of drug resistance. Initially observed in the late 1950's and early 1960's in South America and Southeast Asia, chloroquine-resistant *Plasmodium* parasites that are associated with the most virulent form of malaria, cerebral malaria, have now spread to all malarious regions of the world. Varney et al. (1994)[55] (1997)[56] and others report a strong correlation between cerebral malaria and neuropsychiatric symptoms, such as poor dichotic listening, 'personality change', depression, and, in some cases, partial seizure-like symptoms. The tropical neuralnesia resulting from the legendary malarial fevers is well known in endemic areas and has been documented throughout history.

Due to the spread of multi-drug resistance, mefloquine is currently the drug of choice in treating malaria. However, this drug is known to cause sleep disturbances, increased dream activity, and cause depression in some individuals.[5] Ototoxicity and central nervous system effects are known to occur with mefloquine therapy and may be as common as 1 in 200 to 1,000 individuals.[14,30,48,58] Resistance to mefloquine is now common and occurs in regions in which the drug is not in general use.

Replacement drugs are urgently needed to treat malaria. The endoperoxides, like artemisinin (derived from a Chinese herbal remedy extracted from the wormwood plant) are being used in other parts of the world for malaria therapy. However, the use of this remedy is limited by reports of ototoxicity and neurotoxic effects of the endoperoxides.[6,7,49] More recently, severe reproductive toxicity in female rats has been reported in animals treated with artesunate and its active metabolite, dihydroartemisinin. These findings are mirrored in reports by others in several different animal models.[9]

Another pharmaceutical used in the treatment of malaria is atovaquone. Atovaquone is combined with the agent proguanil in a formulation known as Malarone® for treatment of malaria. Used alone, resistance to atovaquone occurs rapidly and is linked to specific mutations in the parasite gene encoding cytochrome b, a major transmembrane subunit of the cytochrome $bc_1$ complex central to the redox and proton pumping reactions occurring in the parasite mitochondrion.[26,53] Mutations at or near the ubiquinol binding region of the protein seem to sterically hinder binding of atovaquone, with its rigid and bulky side chain.[23,33] In order for the parasite to survive, such mutations must permit discrimination between the drug and ubiquinol binding to cyt b.

Floxacrine is a drug that was described by Raether of Hoechst in the 1970's and 80's.[38,39,59] This acridinedione is active to some extent in vitro and in vivo against multi-drug resistant *Plasmodium* parasites but development of the drug was abandoned due to unacceptable toxicity. Winkelmann and Raether found that the fully aromatic acridone analog of floxacrine was only slightly active against *Plasmodium* parasites [59] (see their compound #111). The mode of action of floxacrine has not been determined. Suswam et al. have reported a modest cross-resistance between floxacrine and atovaquone in *P. falciparum* isolates and clones.[47]

In spite of all this, the pursuit of products specifically aimed at tropical diseases is not considered to be sufficiently profitable to feature among the research priorities of most pharmaceutical companies.[50,51] The panacea for malaria therapy would be the development of a long-lasting vaccine, but the recent failure of the SPf66 vaccine[1,4] and unrealized potential of newer multi-component DNA vaccines,[12] combine to indicate that a vaccine is a long way from reality.

A need continues to exist in the medical field for the development of safe, inexpensive anti-parasitic agents, especially agents that would be useful against multi-drug-resistant organisms such as *P. falciparum* and *P. vivax*.

SUMMARY

The present invention in a general and overall sense provides new pharmacologically active preparations and methods of making and using these preparations in the treatment of parasitic diseases and infectious diseases.

In some aspects, the invention provides novel chemical molecules having a structure that includes a linear or branched chain fluorinated alkyl or alkoxy moiety attached to a substituted aromatic component. In some embodiments, the fluorinated alkyl or alkoxy moiety comprises an alkoxy tri-fluorinated group, such as a trifluoromethyl ($CF_3$)-containing alkoxy group. In some embodiments, the trifluoromethyl group is located at a terminal end of the alkyl/alkoxy moiety.

A particular structural element of the optimized compounds and derivatives, among others, is the presence of an extended (4 to 14 carbon atoms) linear or branched chain alkyl or alkoxy moiety that is terminated by fluorinated carbon atoms.

In some embodiments, the fluorinated alkyl or alkoxy aromatic compounds, as well as analogs and derivatives thereof, may be further described as having an enhanced anti-parasitic, particularly anti-malarial, activity.

In some embodiments, the anti-malarial activity of the alkyl or alkoxy aromatic compounds may be described as pharmacologically active at very low concentrations in the low nanomolar and sub-nanomolar ranges. In yet other embodiments, the compounds may be described as having a therapeutic index suitable for use as an agent for the prevention and/or treatment of disease, particularly malaria, in vivo without an untoward level of toxicity.

In other aspects, the fluoro-alkyl/alkoxy aromatic compounds presented herein may be described as having a cytostatic or cytocidal activity against fungal organisms.

The substituted fluoroalkyl/alkoxy aromatic compounds, as well as analogs and derivatives thereof, may in some embodiments comprise substituted 4(1H) pyridones. In other embodiments, the substituted fluoro-alkyl/alkoxy aromatic compounds, as well as analogs and derivatives thereof, may comprise quinolones, naphthoquinones, acridones, anthraquinones, or xanthones. A key feature is the presence of at least one carbonyl group on the aromatic moiety.

In a general and overall sense, the fluoro-alkyl/alkoxy aromatic compounds may be described as comprising a basic chemical structure of Formula I:

D-n-QZ wherein QZ is a moiety having a moiety Q and a moiety Z, wherein Q comprises a moiety O, $CH_2$, S, NH; or D, and is a bridging group connecting the moiety Q to a moiety Z; Z comprises a moiety H when Q is D, or Z comprises a linear or branched chain alkyl or alkene moiety of 4 to 14 carbons in length, terminated by one or more fluorine atoms when Q is other than D; D comprises a moeity H, OH, alkyl, alkoxy, halogen, haloalkyl, alkoxy, substituted alkoxy, $NH_2$, alkylamine, dialkylamine, cyclic alkylamine, azido, carboxy, carboxylate, substituted carboxy (ester), carboxamide, cyano, amidino, nitro, —SH, alkylthio, sulfonate, or sulfonamide; and n comprises an aromatic moiety bearing a carbonyl functional group selected from the group consisting of:

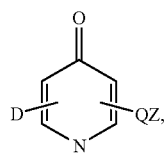
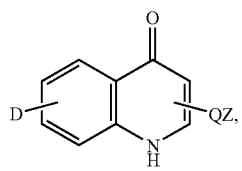

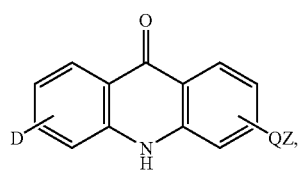

-continued

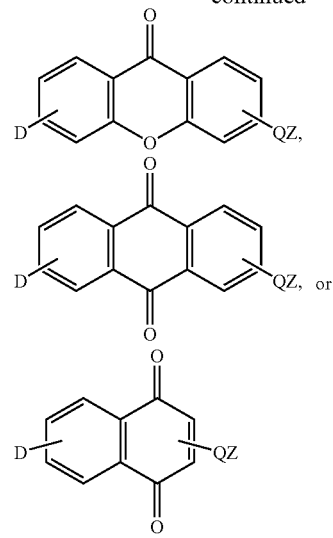

wherein said composition D-n-QZ has an anti-parasitic activity and/or an activity that reduces or otherwise inhibits growth of a microorganism.

In specific embodiments, n is an aromatic ketone. By way of example, these aromatic ketones include 9(10H)-acridones, 4(1H)-quinolones, 4(1H)-pyridones, 1,4-naphthoquinones, 9,10-anthraquinones, xanthones, or 9(10H)-anthrones.

In particular embodiments, Z is a branched, linear or cyclic alkyl or alkene moiety that is substituted at its terminal end with one or more fluorine atoms.

By way of example, but not limited to, the terminal chemical moiety comprises a fluorine-bearing group such as —$CH_2F$, —$CHF_2$, —$CF_3$, —$C_2F_5$, n-$C_3F_7$, i-$C_3F_7$, n-$C_4F_9$, i-$C_4F_9$, or —$SF_5$. In some embodiments, the Z moeity comprises a branched or a straight-chain alkyl or alkene. Where Z is an alkene moiety, it may contain 1 or more double bonds, for example, 2 or 3 double bonds. In each embodiment, there is only a single QZ group attached to the aromatic core component at any available carbon atom. In particular embodiments, D moieties can be at any position on the aromatic core component that is not occupied by QZ, and may further be located at more than one location of an aromatic core component.

In some embodiments, D comprises a moiety that is substituted with an amino group. The D moiety may in some embodiments serve to improve the solubility or molecular electronic characteristics of the molecule.

In some embodiments, and by way of example, Z comprises a moiety that is terminated by a halogen-bearing group, such as —$CF_3$, —$CH_2F$, —$CHF_2$, $C_2F_5$, n-$C_3F_7$, i-$C_3F_7$, n-$C_4F_9$, i-$C_4F_9$, or —$SF_5$.

In all embodiments, Z is attached to Q, and Z is attached to a carbon atom of the aromatic component "n". In essentially all embodiments, Z will be attached to Q.

In some embodiments, Z is attached to Q, and Q positioned at an aromatic carbon atom of n. In particular embodiments, Z comprises an alkyl moiety of 4 to 14 carbons in length, and comprises a terminal carbon having 1 or more fluorine atoms. In particular exemplary embodiments, this terminal fluorine constituent is —$CH_2F$, —$CHF_2$, —$CF_3$, $C_2F_5$, n-$C_3F_7$, i-$C_3F_7$, or n-$C_4F_9$, i-$C_4F_9$, or —$SF_5$.

2-(6,6,6-trifluoro-pentyloxy)-[1,4]naphthoquinone (See FIG. 2)

Other embodiments of the fluoro-alkyl/alkoxy aromatic compounds comprise a structure of Formula I, D-n-QZ, wherein n is a 1,4-naphthoquinone aromatic ring system, and comprises a structure:

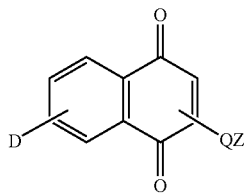

wherein 1 or more of the positions of the aromatic system not otherwise occupied by QZ is D.

In some embodiments, one position of the aromatic system is occupied by a moiety Q, and the Q moiety is an oxygen (O) atom, and further comprises a Z moiety, the Z moiety comprising a halo-alkyl moiety, such as a 5-carbon alkyl terminated by 1 or more fluorine atoms. By way of example, the 5-carbon halo-alkyl may be terminated by 3 fluorine (F) atoms. In some embodiments, this compound is 2-(5,5,5-trifluoro-pentyloxy)-[1,4]naphthoquinone. This compound is further described as having an $IC_{50}$ value of ≈133 nM against a drug sensitive (D6) strain of *Plasmodium falciparum* and against multi-drug resistant strains of *Plasmodium falciparum* (W2, Dd2, 7G8 and Tm93C1088). In these embodiments, placement of the QZ group onto the naphthoquinone ring system improves antimalarial potency by roughly 50-fold (compared to the $IC_{50}$ value for 2-hydroxy-1,4-naphthoquinone which is about 1,800 nM).

2-methyl-3-(11,11,11-trifluoro-undecyl)-7-methoxy-4-(1H)-quinolone (See FIG. 2)

In other embodiments, the fluoro-alkyl/alkoxy aromatic compound comprise a structure of Formula I, D-n-QZ, wherein n comprises a 4(1H)-quinolone aromatic ring system having a structure:

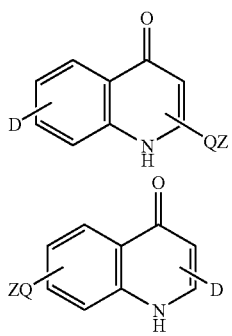

wherein the D moiety is positioned at 1 or more positions of the aromatic ring system not otherwise occupied by QZ, the Q moiety comprises a methylene ($CH_2$) group located at one position of the aromatic ring system not otherwise occupied by D, the Z moiety comprises an eleven (10) carbon alkyl chain that includes 1 or more terminal halogen substitutions, such as fluorine (F) substitutions.

For example, in particular embodiments, the QZ moiety comprises an eleven (11) carbon alkyl that comprises a trifluorine substituted terminal carbon moiety (C11-F3). In particular of these embodiments, this compound is 2-methyl-3-(11,11,11-trifluoro-undecyl)-7-methoxy-4-(1H)-quinolone. This 4(1H)-quinolone compound may be further described as having an $IC_{50}$ of about 0.2 nM against a drug-sensitive strain (D6), and an $IC_{50}$ of about 0.2 nM against a multi-drug resistant strain (W2), of *Plasmodium falciparum*. The presence of the particular QZ moiety as a side chain brings about a dramatic antimalarial enhancement of more than 1,000-fold compared to 2-methyl-7-methoxy-4-(1H)-quinolone ($IC_{50}$>2,500 nM).

3-(6,6,6-trifluorohexyloxy)-6-hydroxyxanthone (See FIG. 2)

Other embodiments of the fluoro-alkyl/alkoxy aromatic compounds comprise a structure of Formula I, D-n-QZ, wherein n is a xanthone aromatic ring system, and comprises a structure:

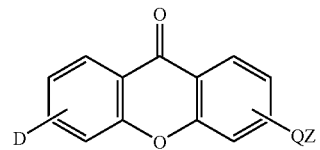

wherein 1 or more of the positions of the aromatic system not otherwise occupied by a QZ moiety is a D moeity.

In some embodiments, one position of the aromatic system is occupied by a Q moeity, wherein the Q moiety comprises an oxygen (O) atom, and a Z moiety, wherein the Z moiety comprises a halo-alkyl moiety, such as a 6-carbon alkyl terminated by 1 or more fluorine atoms. By way of example, the 6-carbon halo-alkyl may be terminated by 3 fluorine (F) atoms. In some embodiments, one position of the aromatic system is occupied by a D moeity, defined as a hydroxy group. In some embodiments, this compound is 3-(6,6,6-trifluorohexyloxy)-6-hydroxyxanthone. This compound is further described as having an $IC_{50}$ value of ≈0.7 μM against a drug sensitive (D6) strain of *Plasmodium falciparum* and against multi-drug resistant strains of *Plasmodium falciparum* (W2, Dd2, 7G8 and Tm93C1088). Thus, placement of the QZ moiety group onto the xanthone ring system improves antimalarial potency by more than 100-fold (as compared to the $IC_{50}$ value for 3,6-dihydroxy-xanthone which is over 100 μM).

3-(6,6,6-trifluorohexyloxy)-6-chloroacridone (See FIG. 2)

Other embodiments of the fluoro-alkyl/alkoxy aromatic compounds comprise a structure of Formula I, D-n-QZ, wherein n is an acridone aromatic ring system, and comprises a structure:

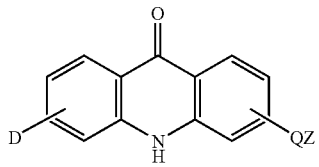

wherein 1 or more of the positions of the aromatic system not otherwise occupied by a QZ moiety comprises a D moiety.

In some embodiments, one position of the aromatic system is occupied by a Q moiety, wherein the Q moiety comprises an oxygen (O) atom, and a Z moiety, wherein the Z moiety comprises a halo-alkyl moiety, such as a 6-carbon alkyl terminated by 1 or more fluorine atoms. By way of example, the 6-carbon halo-alkyl may be terminated by 3 fluorine (F) atoms. In some embodiments, one position of the aromatic system is occupied by a D moiety. wherein the D moiety comprises an hydroxy group. In some embodiments, this compound is 3-(6,6,6-trifluorohexyloxy)-6-chloro-acridone, wherein the chlorine atom represents a D moiety and it is located at position 6 of the central aromatic system. This compound is further described as having an $IC_{50}$ value of 0.16 nM against a drug sensitive (D6) strain of *Plasmodium falciparum* and an $IC_{50}$ value of 0.16 nM against multi-drug resistant strains of *Plasmodium falciparum* (W2, Dd2, 7G8 and Tm93C1088). Thus, placement of the QZ moiety onto the acridone ring system improves antimalarial potency by more than 10,000-fold (as compared to the $IC_{50}$ value for 3-hydroxy-6-chloroacridone which is over 2,200 nM).

3-Amino-5-Methoxy-6-methyl-2-(6,6,6-trifluoro-hexyloxy)-4(1H)-pyridone (See FIG. 2)

In other embodiments, the fluoro-alkyl/alkoxy aromatic compound comprise a structure of Formula I, D-*n*-QZ, wherein n comprises an aromatic pyridone system having a structure:

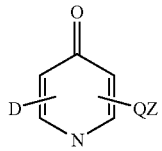

wherein 1 or more of the positions on the aromatic system is occupied by a D moiety or a QZ moiety.

In particular embodiments, the D moiety comprises methoxy ($CH_3O$), methyl ($CH_3$) or $NH_2$, the Q moiety comprises an oxygen (O) atom, and the Z moiety comprises a six (6) carbon alkyl that includes 1 or more terminal halogen substitutions, such as fluorine (F) substitutions. For example, in particular embodiments, the Z moiety is a six (6) carbon alkyl chain that comprises a tri-fluorine substituted terminal carbon moiety (C6-F3). In particular embodiments, the D moiety comprises methoxy ($OCH_3$) at one position, methyl at another position, and $NH_2$ at another position of the aromatic system not occupied by a QZ moiety. In particular of these embodiments, QZ is 6,6,6-trifluoro-hexyloxy. This compound may most specifically be defined as 3-amino-5-methoxy-6-methyl-2-(6,6,6-trifluoro-hexyloxy-4(1H)-pyridone.

6-Methoxy-2-(6,6,6-trifluoro-hexyloxy)-4(1H)-quinolone (See FIG. 2)

In some embodiments, the alkyl/alkoxy aromatic compound comprise a structure of Formula I, D-*n*-QZ, wherein n comprises an aromatic system having a structure:

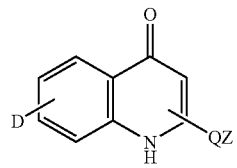

wherein the D moiety is methoxy ($CH_3O$) at one or more positions of the aromatic system, and the Q moiety is an oxygen (O) atom, and the Z moiety is a 6-carbon alkyl chain terminated by a tri-halogenated (tri-fluorinated) moiety.

By way of example, this QZ moiety is a 6,6,6-trifluorohexyloxy group. In a particular embodiment, this compound comprises 6-Methoxy-2-(6,6,6-trifluoro-hexyloxy)-4(1H)-quinolone.

3-carboxamido-6-(6,6,6-trifluoro-hexyloxy)-9-acridone (See FIG. 2)

In some embodiments, the alkyl/alkoxy aromatic compound comprise a structure of Formula I, D-*n*-QZ wherein n is an aromatic acridone system comprising a structure:

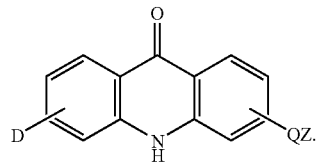

wherein 1 or more positions of the aromatic system that is not otherwise occupied by a QZ moiety is a D moiety. In some embodiments, one of the positions of the aromatic system comprises a D moiety, and the D moiety is $CONH_2$.

In some embodiments, the QZ moiety is 6,6,6-trifluorohexyloxy. In these particular embodiments, the compound may be defined as 3-carboxamido-6-(6,6,6-trifluoro-hexyloxy)-9-acridone.

Generally, the alkyl/alkoxy aromatic compositions include a fluorine atom. In most embodiments, one or more fluorine atom(s) are located on the extended alkyl or alkoxy side chain.

In some embodiments, the alkyl groups of the compounds may be branched or linear alkyl groups and the branched substituents may be connected to form a ring. In some embodiments the alkyl groups may be described as having a fluorine atom located at the terminal end of the alkyl branched or linear chain. The terminal carbon of the branched or linear carbon chain may further be described as including one or more fluorine substitutions. In this regard, some embodiments of the chemical molecule will include 2 or 3 fluorine substituents or more. For example, in some embodiments, the compound comprises a tri-halogen substituted group, such as a tri-fluoromethyl substituted group, $CF_3$.

In some aspects, methods are provided for the treatment and/or prevention of parasitic diseases. In some embodiments, the parasitic diseases may be further described as human parasitic diseases. By way of example, such human or animal parasitic diseases include malaria, toxoplasmosis, amebiasis, giardiasis, leishmaniasis, trypanosomiasis, coccidiosis, caused by organisms such as *Toxoplasma* sp., *Eimeria* sp., *Babesia bovis, Theileria* sp, and also includes infections by helminths, such as ascaris, schistosomes and filarial worms. The present compositions and methods are also effective in the treatment of fungal pathogens including *Pneumocystis carinii, Aspergillus fumigatus*, and others.

In particular aspects, the parasitic diseases may be caused by parasites that cause malaria. Particular species of parasites that are included within this group include all species that are capable of causing human infection. By way of example and not exclusion, such species of parasites include *Plasmodium falciparum, Plasmodium vivax, Plasmodium ovale*, and *Plasmodium malariae*.

In other embodiments, the invention provides for a treatment regimen comprising administering to an animal in need thereof an effective amount of a pharmaceutically acceptable preparation of the compound of Formula I, alone or in combination with another pharmaceutically active component. In some embodiments, a combination of the compound of Formula I may be administered as part of a treatment regimen with quinine, quinones, chloroquine, atovaquone, proguanil, primaquine, amodiaquine, mefloquine, artemisinin, methylene blue, 7-chloro-10-hydroxy-3-(4-trifluoromethylphenyl)-3,4-dihydroacridine-1,9 (2H,10H)-dione (Floxacrine®), pyrimethamine, sulfadoxine, artemether-lumefantrine (Coartem®), dapsone-chlorproguanil (LAPDAP®), artesunate, quinidine, clopidol, pyridone/pyridinol analogs (e.g., clopidol), dihydroartemisinin, atovaquone, Malarone® (mixture of atovaquone and proguanil), an endoperoxide (e.g., artemisinin), or any combination of these.

In yet another aspect, the herein described compounds are formulated into pharmaceutical compositions for administering to subjects in a biologically compatible form suitable for administration in vivo.

In yet other aspects, the invention provides methods for the treatment of fungal infections. By way of example, these fungal infections are human or animal fungal infections, such as *pneumocystis*, and plant fungal infections, such as those that currently compromise various agricultural industries. In particular, the fluoro-alkyl/alkoxy aromatic compounds possess an antifungal activity that may be used to control a number of common plant pathogens that reduce crop yields.

Some of the plants and agricultural crops susceptible to plant pathogens and plant diseases that may be treated with the herein described alkyl/alkoxy aromatic compounds include several important food crops. Some of these important food crops include wheat (wheat rust, rye ergot), peanuts (aflatoxin), potatoes (*Phytophthera infestans*, potato late-blight), peaches (*Monilinia fructicola*, brown rot), grapes (*Uncinula necator*, grapevine powdery mildew), and plants of the genus *Solanum*, including potatoes and tomatoes (late blight fungus) and strawberries (*Botrytis cinerea*, grey mold).

By way of example, the fluoro-alkyl/alkoxy aromatic compounds may be formulated to provide a treatment for application to a plant and/or agricultural crop of interest. Hence, the invention in yet another aspect provides a method of enhancing agricultural crop yield and for treating plant pathogens and inhibiting plant pathogen spread and infectivity. The alkyl/alkoxy aromatic compounds may be used either alone or in combination with other plant pest management treatments. By way of example, other fungicides that may be used in combination preparation with the presently disclosed compounds include sulfur-based preparations (wettable sulfur), sterol inhibitors and strobilurins, as well as a "Bordeaux mixture" (combination of copper sulfate and lime, used to treat late blight fungus).

In yet another aspect, a screening method is provided comprising screening compounds having anti-parasitic activity, particularly anti-malarial, or anti-fungal activity. In some embodiments, the method comprises selecting molecules having a fluoro-alkyl/alkoxy aromatic pharmacophore structure of Formula I as defined herein to provide a pool of candidate anti-parasitic compounds, and selecting candidate compounds having an in vitro anti-Plasmodium activity characterized by an $IC_{50}$ value of 1 µM (micromolar) or less against a drug-sensitive strain of *Plasmodium falciparum*, to provide a pool of candidate anti-parasitic compounds.

The following abbreviations are used throughout the description of the present invention:
BFU-E—burst forming unit, erythroid;
CFU-GM—colony forming unit, macrophage-granulocyte;
$EC_{50}$—effective drug concentration required to decrease parasitemia by 50% relative to control, untreated animals;
FACS—fluorescence activated cells sorting/scanning;
$IC_{50}$—drug concentration required to inhibit parasite growth by 50% relative to control values;
i.p.—intraperitoneal;
i.v.—intravenous;
IVTI— in vitro therapeutic index; calculated from the ratio of $IC_{50}$ value based on the cytotoxicity observed in the blastogenesis assay and the anti-malarial potency against the D6 strain (non-drug resistant, drug sensitive) of *P. falciparum*.
MSF—malaria specific fluorescence assay;
PRBC—parasitized red blood cell(s);
RFU—relative fluorescence units

BRIEF DESCRIPTION OF THE DRAWINGS

The invention will be described in conjunction with the accompanying drawings, in which.

DETAILED DESCRIPTION

Figure 1:
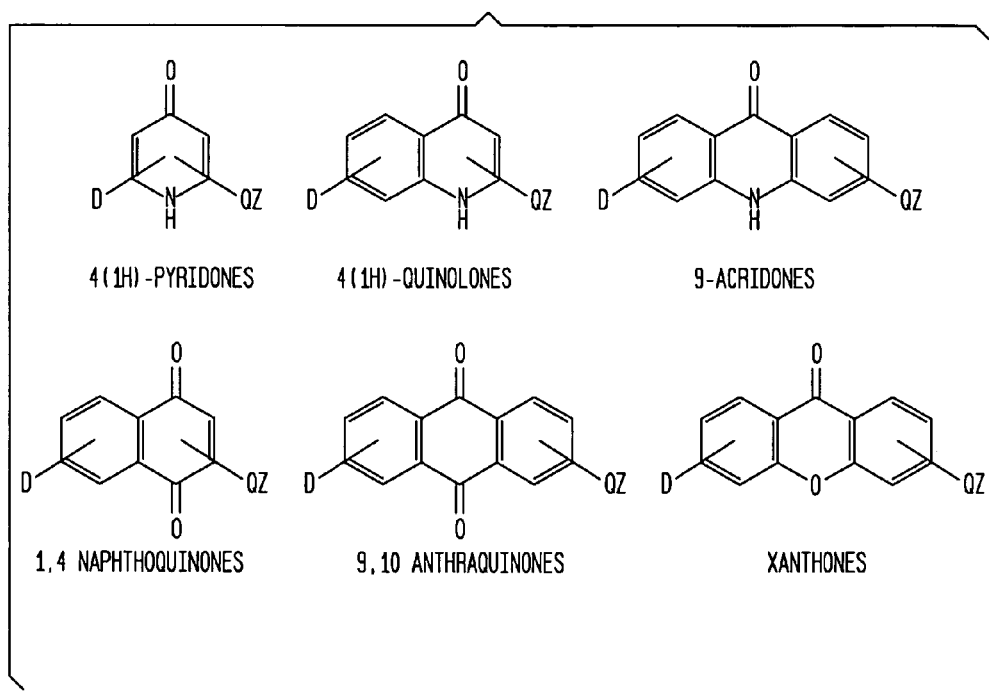
FIG. 1, in accordance with the generalized formulation of the subject compounds, i.e., "D-n-QZ", illustrates the unique and defining structural features of the aromatic fluoro-alkyl/alkoxy compounds of this invention. These include generalized structures for optimized 4(1H)-pyridones, 4(1H)-quinolones, 9(10H)-acridones, 1,4-naphthoquinones, 9,10-anthraquinones, and 9-xanthones.
Figure 2:
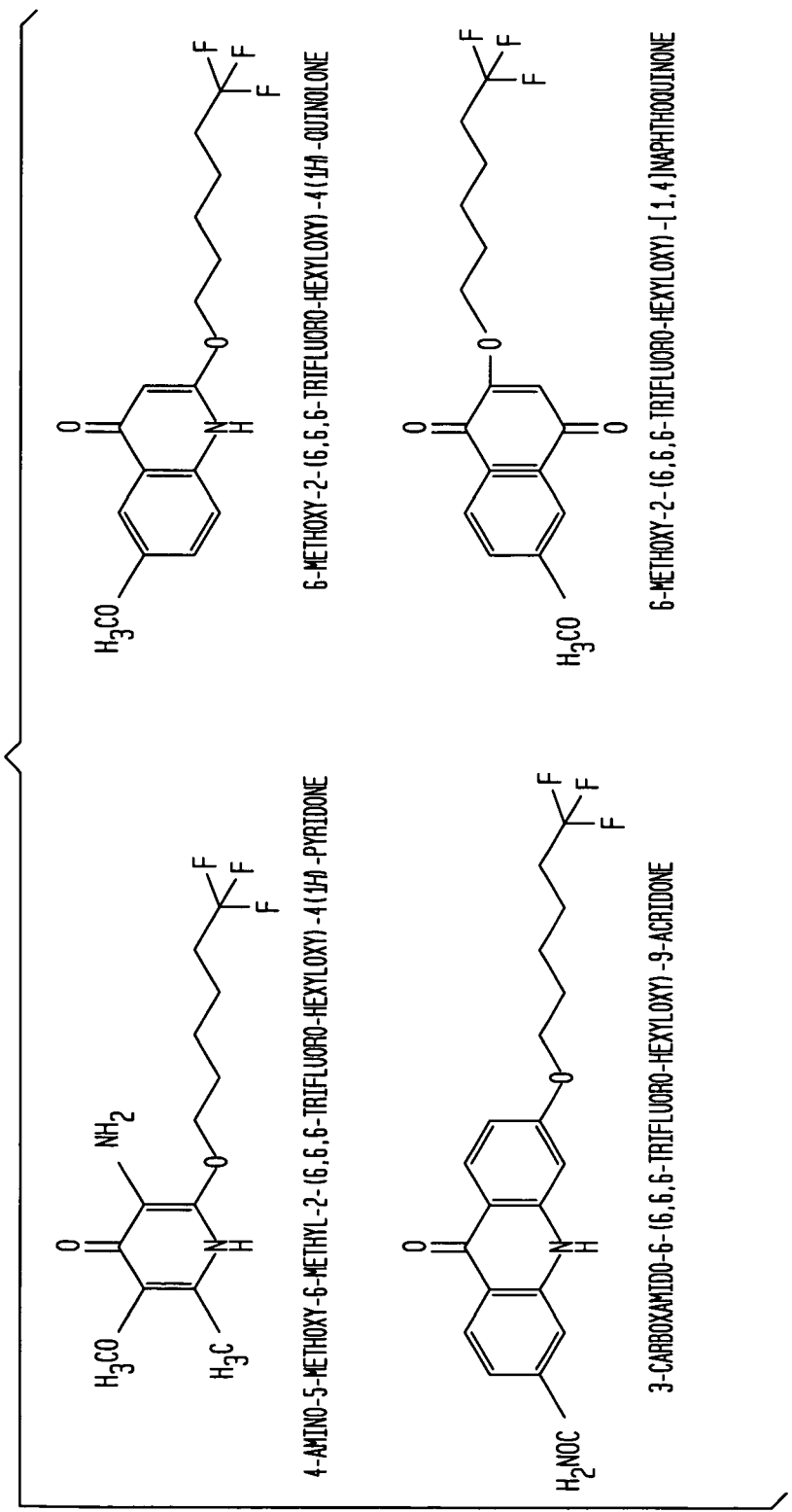
FIG. 2, in accordance with one embodiment of the invention, chemical structures for prototypic compounds of the fluoro-alkyl/alkoxy aromatic compounds of the invention. These include 3-Amino-5-methoxy-6 methyl-2-(6,6,6-trifluoro-hexyloxy)-4(1H)-pyridone, 6-Methoxy-2-(6,6,6-trifluoro-hexyloxy)-4(1H)-quinolone, 3-Carboxamido-6-(6,6,6-trifluoro-hexyloxy)-9-acridone, and 6-Methoxy-2-(6,6,6-trifluoro-hexyloxy)-[1,4]naphthoquinone.
Figure 3:
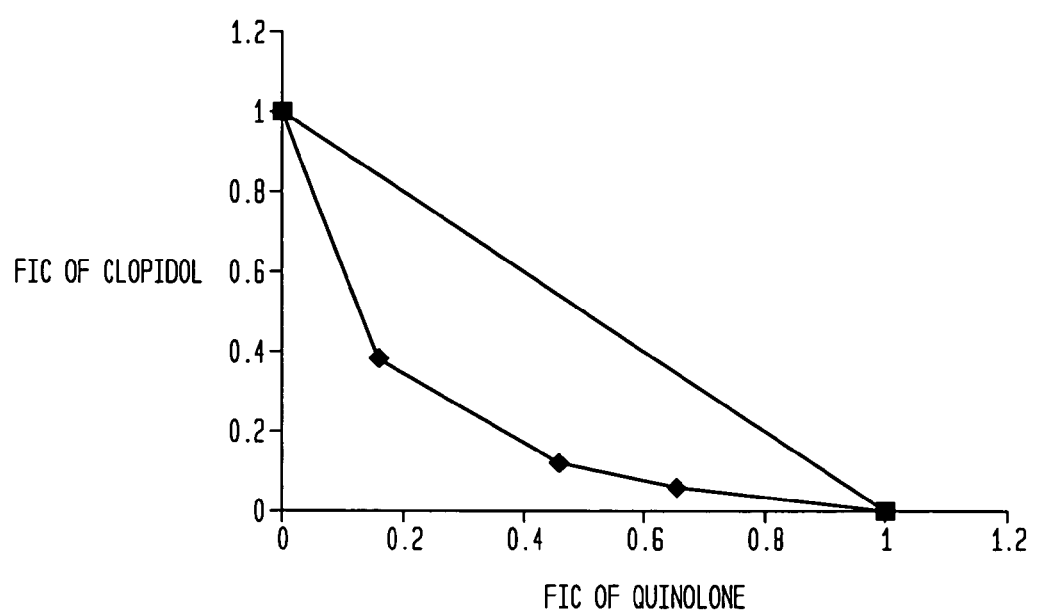
FIG. 3, in accordance with one embodiment of the invention, presents an example of a claimed compound, i.e., 2-methyl-3-(6,6,6-trifluorohexyl)-7-methoxy-4(1H)-quinolone, inhibiting oxygen consumption by *Plasmodium* parasitized red blood cells in similar fashion to atovaquone, an established antimalarial drug. In contrast, NAP 005 (i.e., 2-(5,6,6,6-tetrafluoro-5-trifluoromethyl-hexyloxy)-[1,4]naphthoquinone), another example of a compound that falls within the "D-n-QZ" general chemical structure, does not inhibit oxygen consumption by parasitized red cells, and is also a potent antiplasmodial agent.
Figure 4:
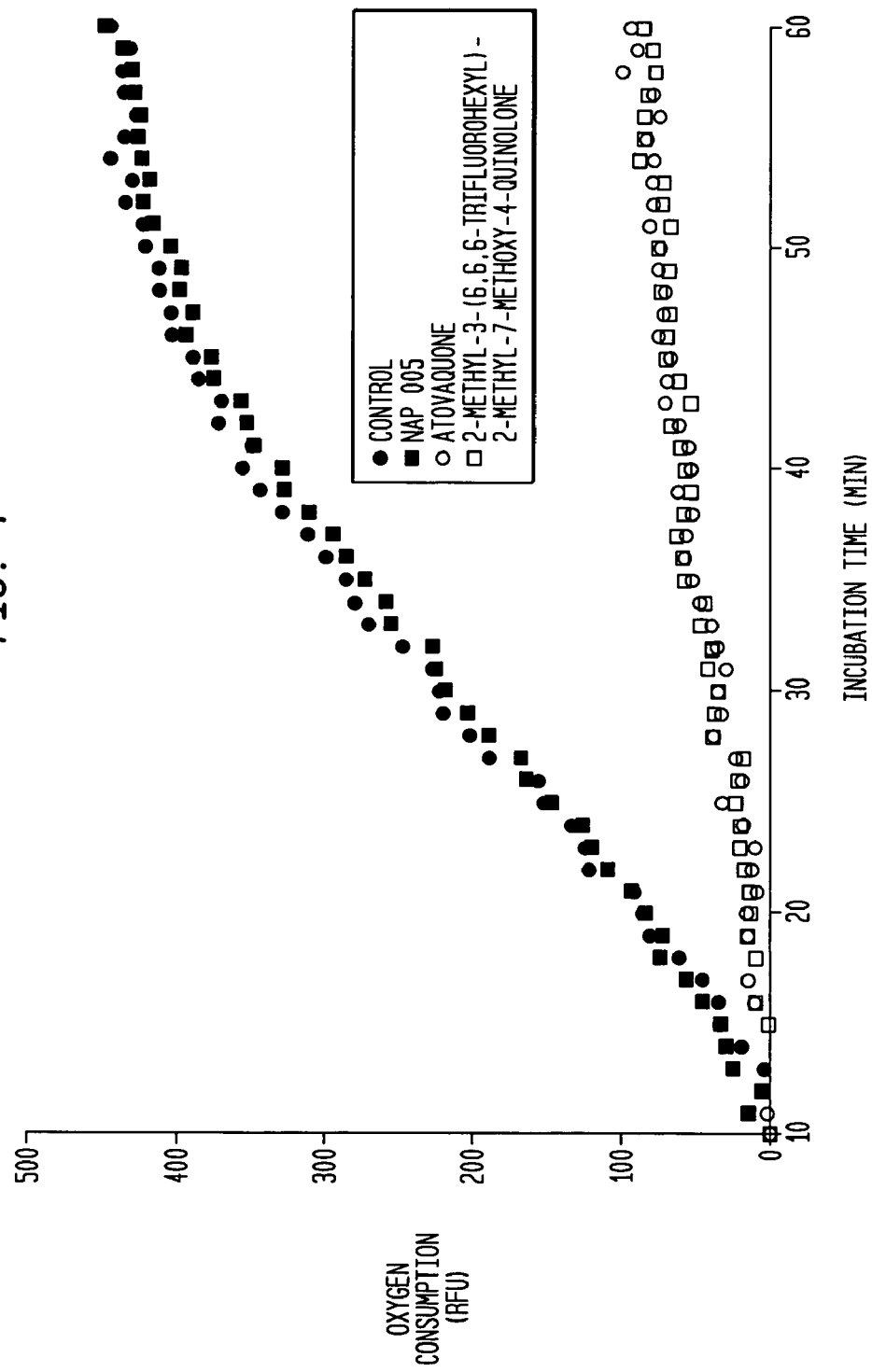
FIG. 4. in accordance with one embodiment of the invention, an example of a claimed compound, i.e., 2-methyl-3-(6,6,6-trifluorohexyl)-7-methoxy-4(1H)-quinolone, acting in synergy with clopidol against multidrug resistant *P. falciparum* strain Dd2 in vitro.

It is advantageous to define several terms before describing the invention. It should be appreciated that the following definitions are used throughout this application.

DEFINITIONS

Where the definition of terms departs from the commonly used meaning of the term, applicant intends to utilize the definitions provided below, unless specifically indicated.

The term "biologically compatible form suitable for administration in vivo" relates to a form of the fluoro-alkyl/alkoxy aromatic compound or derivative thereof to be administered in which any toxic effects are outweighed by the therapeutic effects. The compounds and preparations containing the compounds may be administered to living organisms, including humans, animals and plants.

The term "a", "an" and "the" include reference to the plural unless the context as herein represented clearly indicates otherwise.

The term "alkyl" refers to a carbon chain of 1, 2, 3, 4, 5, 6, 7, 8, 9, 10, or 11, 12 13, 14, 15, or even up to 20 carbons in length.

The term "extended alkyl" refers to a carbon chain of 4, 5, 6, 7, 8, 9, 10, or 11, 12 13, or even up to 14 carbons in length.

The term "anti-parasite activity" is defined as an inhibitory and/or anti-biological activity against a pathogenic organism, such as a parasite cell, including *Plasmodium* and including bacteria and fungi.

The term "drug resistant" relates to an absence of or a reduced inhibitory response to an agent, relative to the response of a non-resistant control organism or cell.

The term "effective" amount relates to a volume, dose or concentration of a haloalkoxy-aromatic ketones, or a composition or preparation containing a haloalkoxy aromatic ketone derivative, that prevents establishment of an infection (e.g., prophylaxis), or growth or provides a detectable decrease in *Plasmodium* growth. By way of example, anti-*Plasmodium* activity may include blockage of invasion of red blood cells or liver cells by the parasite or inhibition of parasite replication within either of these host cells.

A composition that is described herein as "enriched" for a particular pharmacologically or biochemically active agent, for example, is further defined as a composition that contains a higher concentration of a particular fluoro-alkyl/alkoxy aromatic compound or derivative as defined herein, or demonstrates a greater pharmacological or biochemical activity associated with the particular alkyl/alkoxy aromatic compound or derivative and/or preparation, relative to the concentration or detectable associated pharmacological or biochemical activity of that fluoro-alkyl/alkoxy aromatic derivative and/or preparation as it is otherwise found in nature and/or in a non-purified or non-screened compositional form. By way of example, a pharmacologically or biochemically active agent may comprise a fluoro-alkyl/alkoxy aromatic compound or derivative or preparation as described herein.

The term "essentially free" of cytotoxic activity against white blood cells, or a subtype of white blood cells, e.g., lymphocytes, is further described as having a de minimus (for example, 10% or 5% or less) cytotoxic or inhibitory activity from the pharmacological activity of the alkyl/alkoxy aromatic compound or derivative. For example, a de minimus cytotoxic or inhibitory activity may comprise 20% or less, or in some cases, 10% or less, of a detectable cytotoxic or inhibitory activity in a culture of white blood cells attributable to the pharmacological activity of the fluoro-alkyl/alkoxy aromatic ketone, at a relatively high concentration of the compound. By way of example, a relatively high concentration of the compound may comprise about 10 μM (10 micromolar) or more.

The term "halogen" is defined as a fluorine, bromine, iodine or chlorine atom.

The term "higher alkyl" relates to a carbon chain, branched or linear, that is 4 to 14, or more carbons in length.

The term "inhibition" relates to any quantitative or qualitative reduction including prevention of infection and/or complete killing of an invading organism, relative to a control. ("Control" as a non-treated or control treated value.)

The term "invading" relates to a pathological activity of an organism against a healthy cell, a population of healthy cells, or whole organism.

The term "lower alkyl" relates to a carbon chain, branched or linear, that is 2 to 3 carbons in length. As used in the description of the present invention, the term "lower alkyl" refers to substituents having alkyl groups, i.e., an alkyl chain, of 3 or fewer carbon atoms.

The term "pharmacologically active amount" relates to an amount of a particular fluoro-alkyl/alkoxy aromatic compound or a tautomer thereof, as defined herein or fluoro-alkyl/alkoxy aromatic compound in combination with another agent that provides a detectable reduction in parasitic activity in vitro, or diminishes the likelihood of emergence of drug resistance.

The terms "pharmacological activity" and "biochemical activity" relates to a pharmacologically or biochemically detectable change in a cell or population of cells that is attributable to the presence or production of a compound either in vitro or in vivo (in cellulo).

The term "pharmacophore" for purposes of describing the present invention, is defined as a molecular framework that is part of a compound that possesses one or more essential features of a drug that is capable of inhibiting an invading or offending parasite, organism, or combination thereof.

The term "therapeutically active amount" relates to an amount effective to achieve a desired result. The therapeutically active amount may, for example, vary according to factors such as the disease state, age, sex, and weight of an organism, animal or individual, and the relative potency of the compound to elicit a desired response in or on an organism, animal or human individual. A dosage regimen may be adjusted to provide an optimum therapeutic response. For example, several different doses may be administered daily or the dose maybe proportionally reduced as indicated by the exigencies of the therapeutic situation.

DESCRIPTION

While the present invention is not necessarily limited to such applications, various aspects of the invention may be appreciated through a discussion of the several examples presented below using this context.

Example 1

Synthesis of 2-(5,5,5-trifluoropentyloxy)-1,4-naphthoquinone

The present example demonstrates a method by which the compounds of the present invention may be synthesized. One unique structural feature, among others, of the pharmacophore presented is the presence of a long alkyl or alkoxy side chain bearing one or more fluorine atoms on the terminal carbon atom(s).

For preparation of 2-(5,5,5-trifluoropentyloxy)-1,4-naphthoquinone: 2-hydroxy-naphthoquinone (1.36 g), 5,5,5-trifluoropentanol (1.30 g), benzene (50 ml) and 10 ml of concentrated hydrochloric acid were heated to boiling for 24 hours. A color change from brick-red to orange occurred. Upon cooling, 2-hydroxy-naphthoquinone crystallized out. The filtrate was evaporated, giving 330 mg of a crystalline residue. It appeared to be a 1:1-complex of 2-OH— and 2-O$(CH_2)_4CF_3$-1,4-naphthoquinone. A sample was decomposed in aqueous KOH, and the turbid mixture was extracted with ethyl acetate, the extract shaken 3 times with an equal volume of water, and the organic layer evaporated. 100 mg of the initial product resulted in 54 mg of product, which is (by g.c.-m.s., $^1$H-n.m.r. spectroscopy) 2-(5,5,5-trifluoropentyloxy)-1,4-naphthoquinone, orange needles, m.p.=108° C.

Example 2

Synthesis of 3-(6,6,6-trifluorohexyloxy)-6-hydroxyxanthone

To 3,6-dihydroxy-xanthone (0.58 g, 1 equivalent) is added 10 ml of ethanol, then 117 mg of KOH 0.8 equivalents), followed by 0.58 g of $CF_3(CH_2)_5Br$ (1 equivalent); after two hours of boiling this mixture, the pH had dropped to the acidic range, and another 100 mg of KOH was added and heating continued overnight. The cooled mixture was diluted with water (50 ml) and extracted with ethyl acetate (3×50 ml), the combined extracts washed with 5 ml of water and brought to dryness. Separation of the 3-component mixture was achieved by chromatography (100 g of silica gel, column diameter 5 cm) with solvents of increasing polarity: Solvents used: ethyl acetate (A), hexane (isomeric mixture) (B), ethanol (C)

| Volume ratio | A:B:C: | Volume | Effect |
|---|---|---|---|
| 1.: | 1:10:0 | 600 ml | no elution |
| 2.: | 2:3:0 | 300 ml | Compound I |
| 3.: | 5:9:1 | 650 ml | Compound II |

The third component, the starting dihydroxyxanthone, was not eluted.

Compound I=3,6-bis-(6,6,6-trifluorohexyloxy)-xanthone, white solid, 0.24 g, m.p.=100° C.

Compound II=3-(6,6,6-trifluorohexyloxy)-6-hydroxyxanthone, white solid, 0.43 g, m.p.=191° C.

Example 3

Preparation of a compound of the "D-n-QZ" formulation wherein the 0 bridging atom is a methylene group: 2-Methyl-3-(11,11,11-trifluoro-undecyl)-7-methoxyauinolone This method utilizes the "Konrad-Limpach reaction", which consists of condensing a substituted (position 2) acetoacetic ester with an aniline, providing a 2-alkyl-3-phenylamino crotonic ester (alternatively formulated as a Schiff base) followed by ring-closure in a high-boiling solvent (Dowtherm A, boiling (atm. p) at about 250° C.). An exemplary reaction is presented below.

Ethyl 2-(11,11,11-trifluoro-undecyl)-acetoacetate is obtained by heating at reflux temperature for 20 hours in 75 ml ethanol, the sodium derivative of ethyl acetoacetate (from 1.60 g ester+0.28 g of Na, first dissolved in ethanol), and 3.45 g of $CF_3(CH_2)_{10}Br$. After this period, the alcohol was evaporated and then water (50 ml) was added to the residue and the product extracted with ethyl acetate (1×40, 1×30 ml), the extracts combined and the solvent evaporated.

The crude ethyl 2-(11,11,11-trifluoroundecyl)-acetoacetate was heated to reflux with 60 ml of benzene, 1.30 g of m-anisidine, and 3 drops of concentrated hydrochloric acid for five hours with continuous removal of water. After this time the solvent was removed, the residue dissolved in =10 ml of Dowtherm A, and the entire solution dropped into 60 ml of boiling Dowtherm A within 2 minutes and kept at boiling for 5 minutes. Since after cooling it is common for no product to crystallize out of solution, about 200 ml of hexane was added. After standing overnight, a crystalline precipitate had formed which was filtered off and washed with a small amount of acetone. Recrystallization ($1^{st}$ alcohol, $2^{nd}$ acetone) provides 0.37 g of whitish shiny soft crystals, pure by thin-layer chromatography, and $^1$H-n.m.r. spectroscopy which also shows the expected spectral pattern for this compound.

Example 4

Chemical synthesis of 3-(6,6,6-trifluorohexyloxy)-6-chloroacridone 3-hydroxy-6-chloroacridone (594 mg) was stirred in 10 ml of methanol, and 5 ml of methanolic KOH (30 mg/ml) was added (1 equiv. base), whereupon complete dissolution occurred. 1-Bromo-5-trifluoromethylpentane (2.03 g, 3 equiv.) was added and the solution heated at 70° C. overnight, forming a fine solid precipitate; after cooling, 0.35 g of pale yellow powder was collected by filtration. When the filtrate is heated another 2 days, the same quantity of product may be isolated in addition. The crude product was crystallized from methanol. Analogous procedures can be applied for preparation of compounds with the $O(CH_2)_3CF_3$, $O(CH_2)_4CF_3$, $O(CH_2)_7CF_3$, and $O(CH_2)_{10}CF_3$— side chains and including aromatic ketone derivatives bearing $O(CH_2)C_2F_5$ and $O(CH_2)C_3F_7$ side chains.

General procedure for $CF_3(CH_2)_nBr$, ω-(Trifluoromethyl) alkylbromide (used in the above procedure): These compounds are prepared by heating co-bromoalkanoic acids with about 2.2 equivalents of $SF_4$ in a steel bomb tube at 115-125° C. overnight; the HF formed in the initial step of forming the acid fluoride sufficed as catalyst. Larger preparations required neutralization of the HF in the crude product;

smaller amounts were directly distilled without the neutralization step. All of them are pale yellow mobile liquids.

Example 5

Aromatic Core Substituted Compounds

The aromatic core nucleus is demonstrated in the present example as part of additional exemplary compounds. The present example demonstrates that the aromatic nucleus is a potent and selective pharmacophore model that may be used in the development of highly potent and selective anti-malarial agents.

The fluorine (F) substituted alkyl side-group may be prepared to take several forms. Examples of these appear in Table 1.

TABLE 1

1. 2-(8,8,8-trifluorooctyloxy)-5-amino-4(1H)pyridone
2. 2-(8,8,8-trifluorooctyloxy)-5-hydroxy-4(1H)pyridone
3. 2-(8,8,8-trifluorooctyloxy)-5-methoxy-4(1H)pyridone
4. 2-(8,8,8-trifluorooctyloxy)-5-carboxy-4(1H)pyridone
5. 2-(8,8,8-trifluorooctyl)-5-carboxy-4(1H)pyridone
6. 3-(5,6,6,6-tetrafluoro-5-trifluoromethyl-hexyloxy)-4(1H)pyridone
7. 2-(5,6,6,6-tetrafluoro-5-trifluoromethyl-hexyloxy)-6-hydroxy-4(1H)pyridone
8. 3-(5,6,6,6-tetrafluoro-5-trifluoromethyl-hexyloxy)-5-hydroxy-4(1H)pyridone
9. 2-(9,9,9-trifluorononyloxy)-5-hydroxy-4(1H)pyridone
10. 2-methy-3-amino-7-(7,7,7-trifluoroheptyloxy)-4(1H)-quinolone
11. 3-hydroxy-6-(6,6,6-trifluorohexyloxy)-xanthone
12. 2-(6,6,6-trifluorohexyloxy)-1,4-naphthoquinone
13. 2-(6,6,6-trifluorohexyloxy)-5-hydroxy-1,4-naphthoquinone
14. 2-(6,6,6-trifluorohexyloxy)-5-methoxy-1,4-naphthoquinone
15. 6-hydroxy-2-(6,6,6-trifluorohexyloxy)-9,10-anthraquinone
16. 3-(6,6,6-trifluorohexyloxy)-9-(10H)-acridone
17. 3-(6,6,6-trifluorohexyloxy)-6-hydroxy-9(10H)-acridone.
18. 3-carboxymethyl ester-7-(6,6,6-trifluorohexyloxy)-4(1H)-quinolone
19. 7-(6,6,6-trifluoro-hexyloxy)-4(1H)-quinolone-3-carboxylic acid (2-hydroxy-ethyl)-amide

Example 6

Solubility Enhancement of Fluoro-Alkyl/Alkoxy Aromatic Compounds

The present example is provided to describe several techniques that may be used to increase the in vivo solubility of the alkyl/alkoxy aromatic compounds of the present invention.

1. Addition of Polar Groups:

The addition of hydroxy (OH)— groups at various sites of the fluoro-alkyl/alkoxy aromatic compounds is anticipated to increase the solubility of the compounds disclosed herein due to improved hydrogen bonding with water in the aqueous environment of the biological system. Addition of other polar chemical moieties can also improve the aqueous solubility of the fluoro-alkyl or alkoxy compounds of this invention. Groups that engage in hydrogen bonding as so-called "hydrogen bond donors" or "hydrogen bond acceptors" improve aqueous solubility due to improved interaction with water in the biological system. Apart from hydroxy, other prototypical examples of such polar groups include (but are not limited to): amino, alkylamino, dialkylamino, amido, carboxy, carboxy ester, sulfonyl, sulfonamide and azido.

2. Halo-Alkene Substituted Groups:

The incorporation of double bonds into the fluorinated alkyl chains, may improve aqueous solubility and drug bioavailability, improving the balance of a drug's lipid solubility (passage across or into biological membranes) vs. water solubility.

3. Bio-Isostere Substitution:

An additional approach at improving solubility and bioavailability of an alkyl/alkoxy aromatic compound according to the present invention includes the placement of a bio-isostere onto the aromatic ring(s) of the compound. By way of example, these include hydroxyl, methoxy, carboxy, substituted carboxy (e.g. ester), amino (or substituted amine, e.g. dimethylamino) nitro, amidino, cyano, alkylthiosulfate, sulfonate and sulfonamide groups. By way of example, such bio-isostere groups are included within the list of D components of Formula 1.

In some embodiments, the bio-isosteric group may be represented as the D component of Formula I and this group may be placed at any carbon atom of the aromatic core part of the molecule that is not otherwise occupied by the single QZ component. In some of these particular embodiments, the bioisosteric group is a chlorine atom or a hydroxy group.

In yet other embodiments, the solubility of the fluoro-alkyl/alkoxy aromatic compound may be improved by modifying the structure to include an N-10 carbamate ester such as of choline or succinate. This particular type of substitution is also expected to improve the targeting of the compound to the invading organism.

In yet other embodiments, the solubility of the fluoro-alkyl/alkoxy aromatic compound or derivative may be improved by the addition of a hydroxyl group at the ring nitrogen atom of the pyridone, quinoline, or acridone nucleus.

The substituted compounds as described under 1, 2 and 3 above can be tested for anti-malarial activity using the D6 strain (chloroquine sensitive, mefloquine resistant) and multi-drug resistant *Plasmodium falciparum* strain W2 (resistant to chloroquine, pyrimethamine and sulfadoxine, among others). The $IC_{50}$ for each of these compounds against both the drug sensitive strain (D6) and the multi-drug resistant strain (W2) of *Plasmodium falciparum* is determined according to the procedure described herein.

Solubility of each of these compounds is assessed by calculating the logP and/or ClogP value for each compound. A generally acceptable solubility range for an optimized fluoro-alkyl/alkoxy aromatic compound is a ClogP value at or below 5.

The ClogP value is a measure of differential solubility of a compound in two solvents. The log ratio of the concentrations of the solute in the solvent is called LogP or the Partition Coefficient. The most well known of these partition coefficients is the one based on the solvents n-octanol and water. The octanol-water partition coefficient is a measure of the hydrophobicity and hydrophilicity of a substance. In the context of drug-like substances, hydrophobicity is related to absorption, bioavailability, hydrophobic drug-receptor interactions, metabolism and toxicity. The classical and most reliable method of LogP determination is the Shake flask method, which consists of mixing a known amount of solute in a known volume of octanol and water, then measuring the distribution of the solute in each solvent. The most common method of measuring the distribution of the solute is by UV/VIS spectroscopy.

Another method for determining logP uses high-performance liquid chromatography. The logP of a solute can be determined by correlating its retention time with similar compounds with known logP values.

Now that so many compounds have been analyzed for logP, it is possible to predict logP values by computational means with high accuracy. Computer software, such as CHEMDRAW by Cambridgesoft software, is capable of predicting logP based on structural fragmentation resulting in values that have been calculated. Such calculations yield ClogP values.

Example 7

In Vitro Anti-Malarial Activity of Fluoro-Alkyl/Alkoxy Containing Compounds, Including Substituted Acridones, Naphthoquinones, Xanthones, and Quinolones The present example is provided to detail the methods that have been used to assess the in vitro activity of the aromatic compounds, particularly aromatic ketones of the D-n-QZ formulation.

Parasite Culture and Passage:

Four different laboratory strains of *P. falciparum* were cultured in human erythrocytes by standard methods under a low oxygen atmosphere (5% $O_2$, 5% $CO_2$, 90% $N_2$) in an environmental chamber. The culture medium was RPMI 1640, supplemented with 25 mM Hepes buffer, 25 mg/liter gentamicin sulfate, 45 mg/liter hypoxanthine, 10 mM glucose, 2 mM glutamine, and 0.5% Albumax II (complete medium). The parasites were maintained in fresh human erythrocytes suspended at a 2% hematocrit in complete medium at 37° C. Stock cultures were sub-passaged every 3 to 4 days by transfer of infected red cells to a flask containing complete medium and uninfected erythrocytes.

Method for In Vitro Screening of Compounds for Antimalarial Potency:

In vitro antimalarial activity of the test compounds was assessed by a fluorescence-based method described previously (Smilkstein et al., 2004, Antimicrobial Agents and Chemotherapy, Vol. 48, pgs. 1803-1806) (reference format?). The studies were set up in triplicate in 96 well plates with two-fold dilutions of each test compound across the plate in a total volume of 100 μl and at a final red blood cell concentration of 2% (v/v). Stock solutions of each drug were prepared by dissolving in DMSO at 10 mM. The dilution series was initiated at a concentration of 1 μM and the experiment was repeated beginning with a lower initial concentration for those compounds in which the $IC_{50}$ value was below 10 nM. In every case, an additional determination was performed to ensure bracketing of the $IC_{50}$ value by at least an order of magnitude.

Automated pipeting and dilution was carried out by a programmable Precision 2000 robotic station (Bio-Tek, Winooski, Vt.). An initial parasitemia of 0.2% was attained by addition of normal uninfected red cells to a stock culture of asynchronous parasite infected red cells (PRBC). The plates were incubated for 72 hrs at 37° C. in an atmosphere of 5% $CO_2$, 5% $O_2$, and 90% $N_2$. After this period, the SyBrGreen I dye-detergent mixture (100 μl) was added and the plates were incubated at room temperature for an hour in the dark and then placed in a 96-well fluorescence plate reader (Gemini-EM, Molecular Diagnostics) for analysis with excitation and emission wavelength bands centered at 497 and 520 nm, respectively. The fluorescence readings were plotted against the logarithm of the drug concentration and curve fitting by nonlinear regression analysis (GraphPad Prism software) yielded the drug concentration that produced 50% of the observed decline from the maximum readings in the drug-free control wells ($IC_{50}$).

TABLE 2

In vitro antimalarial activity of selected tricyclic derivatives against drug susceptible (D6) and multi-drug resistant (Dd2) strains of *Plasmodium falciparum*\*.

| No. | Compound | D6 $IC_{50}$ nM | Dd2 $IC_{50}$ nM | MSLCs $IC_{50}$ nM | IVTI |
|---|---|---|---|---|---|
| 1. | Acridone | 2,000 | 2.500 | >25,000 | >12.5 |
| 2. | 2-aminoacridone | 50,000 | 50,000 | >25,000 | >0.5 |
| 3. | 2-methoxyacridone | 329 | 271 | >25,000 | >75 |
| 4. | 3-methoxyacridone | 283 | 224 | >25,000 | >88 |
| 5. | 2-hydroxyacridone | 9,000 | 4,400 | >25,000 | >2.8 |
| 6. | 3-hydroxyacridone | 2,000 | 504 | >25,000 | >12.5 |
| 7. | 2-methoxy-6-chloroacridone | 45 | 65 | >25,000 | >556 |
| 8. | 2-hydroxy-6-chloroacridone | 190 | 260 | 24,000 | 126 |
| 9. | 2-methoxy-6-chloro-9-aminoacridine | 18 | 42 | 450 | 25 |
| 10. | 2-(□-bromopentyloxy)-6-chloroacridone | 70 | 152 | 12,000 | 171 |
| 11. | 2-(□-chloropentyloxy)-6-chloroacridone | 46 | 40 | >25,000 | >543 |
| 12. | 2-□-dimethylaminopentyloxy--6-chloroacridone | 67 | 95 | 5,600 | 83 |
| 13. | 3-methoxy--6-chloroacridone | 76 | 192 | >25,000 | >329 |
| 14. | 3-hydroxy-6-chloroacridone | 2,200 | 9,200 | 14,000 | 6.4 |
| 15. | 3-(□-bromopentyloxy)-6-chloroacridone | 27 | 54 | >25,000 | >926 |
| 16. | 3-(□-chloropentyloxy)-6-chloroacridone | 12 | 13 | >25,000 | >2,000 |
| 17. | 3-(4,4,4-trifluorobutyloxy)-6-chloroacridone | 1.0 | 1.2 | >25,000 | >25,000 |
| 18. | 3-(5,5,5-trifluoropentyloxy)-6-chloroacridone | 0.3 | 0.5 | >25,000 | >83,000 |
| 19. | 3-(5,5,5-trifluoropentyloxy)-6-chloroxanthone | 16,000 | 18,000 | >25,000 | >1.6 |
| 20. | 3-(5,5,5-trifluoropentyloxy)acridone | 0.5 | 0.3 | >25,000 | >50,000 |
| 21. | 3-(6,6,6-trifluorohexyloxy)-6-chloroacridone | 0.06 | 0.07 | >25,000 | >416,000 |
| 22. | 2-(6,6,6-trifluorohexyloxy)-6-chloroacridone | 10 | 15 | >25,000 | >2,500 |
| 23. | 3-(5,5,6,6,6-pentafluoro-hexyloxy)-6-chloroacridone | 0.02 | 0.02 | >25,000 | >100,000 |
| 24. | 3-(5,6,6,6-tetrafluoro-5-trifluoromethyl-hexyloxy)-6-chloroacridone | 0.0015 | 0.0008 | >25,000 | >100,000 |
| 25. | 2-(6,6,6-trifluorohexyloxy)acridone | 36 | 49 | >25,000 | >694 |
| 26. | 3-(6,6,6-trifluorohexyloxy)acridone | 0.43 | 0.015 | >25,000 | >58,000 |
| 27. | 4-(6,6,6-trifluorohexyloxy)acridone | 446 | 515 | >25,000 | >56 |
| 28. | 3-(8,8,8-trifluorooctyloxy)-6-chloroacridone | 0.16 | 0.17 | >25,000 | >100,000 |
| 29. | 3-(8-hydroxyoctyloxy)-6-chloroacridone | 2.2 | 3.5 | >25,000 | >11,000 |
| 30. | 3-(11,11,11-trifluoro-undecyloxy)-6-chloroacridone | 0.023 | 0.025 | >25,000 | >100,000 |
| 31. | 3-(5,5,5-trifluoropentyloxy)-6-chloro-10-N-methylacridone | 4,000 | 3,500 | >25,000 | >6.25 |

TABLE 2-continued

In vitro antimalarial activity of selected tricyclic derivatives against drug susceptible (D6) and multi-drug resistant (Dd2) strains of Plasmodium falciparum*.

| No. | Compound | D6 IC$_{50}$ nM | Dd2 IC$_{50}$ nM | MSLCs IC$_{50}$ nM | IVTI |
|---|---|---|---|---|---|
| 32. | 3-(6,6,6-trifluorohexyloxy)-6-chloro-9-aminoacridine | 2.9 | 10 | 250 | 86 |
| 33. | 3-(6,6,6-trifluorohexyloxy)-6-nitro-acridone | 3.2 | 5.8 | >25,000 | >7,800 |
| 34. | 3-(6,6,6-trifluorohexyloxy)-6-amino-acridone | 0.018 | 0.025 | >25,000 | >100,000 |
| 34. | 2-hydroxy-1,4-naphthoquinone | 1,800 | 1,800 | >25,000 | >13.9 |
| 35. | 2-(5,5,5-trifluoropentyloxy)-1,4-naphthoquinone | 32 | 35 | 14,000 | 437.5 |
| 36. | chloroquine | 7.8 | 102 | 3,900 | 500 |
| 37. | quinine | 11 | 68 | 23,000 | 2,091 |
| 38. | mefloquine | 5.9 | 8.8 | 4,800 | 813 |
| 39. | artemisinin | 0.65 | 0.9 | >25,000 | >38,000 |

*Data are the average of at least 3 independent experiments, each performed in triplicate with the aid of a Precision 2000 robotic pipeting station. IC$_{50}$ values were determined by the MSF assay. Results did not vary by more than 15% between experiments.
MSLCs = Murine splenic lymphocytes. Cytotoxicity was determined using a 24-hr MSLCs-concanavalin A induced proliferation assay using the Alamar Blue fluorescence method.
IVTI = in vitro therapeutic index calculated from the ratio of IC$_{50}$ values based on the cytotoxicity observed in the blastogenesis assay and the antimalarial potency against the D6 strain of P. falciparum.
NT = not tested.

*Data are the average of at least 3 independent experiments, each performed in triplicate with the aid of a Precision 2000 robotic pipeting station. IC$_{50}$ values were determined by the MSF assay. Results did not vary by more than 15% between experiments. MSLCs=Murine splenic lymphocytes. Cytotoxicity was determined using a 24-hr MSLCs-concanavalin A induced proliferation assay using the Alamar Blue fluorescence method. IVTI=in vitro therapeutic index calculated from the ratio of IC$_{50}$ values based on the cytotoxicity observed in the blastogenesis assay and the antimalarial potency against the D6 strain of P. falciparum. NT=not tested.

As shown in Tables 2, 3, and 4, the most potent compounds share a unique and defining structural element in the presence of an extended alkyl group terminated by one or more $CF_3$ groups. From the data presented in the table, at least one optimal location of the $CF_3$ containing alkyl element differs depending on the nature of the central aromatic ketone. For example, for the acridone nucleus, the optimal location of the fluoro-alkyl/alkoxy group is at the 3 position. This may be the case for 4(1H)-quinolone system as well, although quinolones bearing the haloalkoxy group at the 7 position also exhibit significant potency. Naphthoquinones with the QZ substituent at the 2-position exhibit remarkable antiparasitic activity that is enhanced by 50 to 100-fold over the potency of the unsubstituted 2-hydroxynaphthoquinone.

This is especially evident for 2-position haloalkoxynaphthoquinones, i.e., where "Q" is an oxygen atom. Addition of an extended fluoro-alkoxy moiety to the 3-position of the tricyclic xanthone and acridone systems improved the antimalarial inhibitory potency of the aromatic ketone by at least 100-fold against a panel of Plasmodium falciparum strains (D6, W2, Dd2, 7G8, and Tm93-C1088) harboring resistance to multiple therapeutic agents including chloroquine, quinine, mefloquine, pyrimethamine and atovaquone. With IC$_{50}$ values in the low and sub-nanomolar range, our most active compounds are more potent (in vitro) than many presently used clinical drugs (including the quinolines and endoperoxides).

TABLE 3

Superior anti-malarial potency of omega-trifluoromethyl-alkyl and haloalkoxy-4(1H)-quinolones.

| # | Compound Name | D6 IC$_{50}$, nM | Dd2 IC$_{50}$, nM | MSLCs IC$_{50}$, nM | IVTI |
|---|---|---|---|---|---|
| 40 | 7-methoxy-4(1H)-quinolone | >2,500 | | >25,000 | NA |
| 41 | 3-carboxyethylester-7-methoxy-4-(1H)-quinolone | 440 | | >25,000 | 56.8 |
| 42 | 7-methoxy-3-carboxy-4-(1H)-quinolone | >2,500 | | >25,000 | NA |
| 43 | 2-methyl-7-methoxy-4-(1H)-quinolone | 7,000 | 13,700 | >25,000 | >3.5 |
| 44 | 2-methyl-3-(6,6,6-trifluorohexyl)-7-methoxy-4(1H)-quinolone | 10.2 | 12.8 | >25,000 | ≈2,000 |
| 45 | 2-methyl-3-(11,11,11-trifluoro-undecy1)-7-methoxy-4(1H)-quinolone | 0.2 | 0.36 | >25,000 | >100,000 |
| 46 | 3-carboxyethy1-7-(6,6,6-trifluorohexyloxy)-4-(1H)-quinolone | 1.2 | 1.2 | >25,000 | >20,000 |

*Data are the average of at least 3 independent experiments, each performed in triplicate with the aid of a Precision 2000 robotic pipeting station. IC$_{50}$ values were determined by the MSF assay (Smilkstein et al., AAC, 2004).
MSLCs = Murine splenic lymphocytes. Cytotoxicity was determined using a 48-hr MSLCs-concanavalin A induced proliferation assay using the Alamar Blue fluorescence method.
IVTI = in vitro therapeutic index calculated from the ratio of IC$_{50}$ values of the cytotoxicity observed in the blastogenesis assay and antimalarial potency against the D6 strain of P. falciparum.
NA = not applicable;
ND = not determined.

*Data are the average of at least 3 independent experiments, each performed in triplicate with the aid of a Precision 2000 robotic pipeting station. IC$_{50}$ values were determined by the MSF assay (Smilkstein et al., AAC, 2004). MSLCs=Murine splenic lymphocytes. Cytotoxicity was determined using a 48-hr MSLCs-concanavalin A induced proliferation assay using the Alamar Blue fluorescence method. IVTI=in vitro therapeutic index calculated from the ratio of $IC_{50}$ values of the cytotoxicity observed in the blastogenesis assay and antimalarial potency against the D6 strain of P. falciparum. NA=not applicable; ND=not determined.

It is of interest to consider the nature of the central aromatic unit of the pharmacophore (i.e., the "n" component) and the significance of the haloalkoxy side chain (i.e., the "QZ" component) in drug potency. Replacement of the hydroxy group in 2-hydroxy-1,4-naphthoquinone by a trifluoroalkoxy side chain (see Table 2) improves the antimalarial potency of the parent compound by over 50-fold. A similar antimalarial enhancing effect is seen with the trifluoroalkyl/alkoxy side chain is placed on a quinoline, acridone, xanthone, and anthrone aromatic ring system. Structurally diverse aromatic ketones may therefore be substituted for the centrally located "n" component to expand the structural diversity of this antimalarial class of haloalkoxy and haloalkyl-containing compounds. By altering the structure of the pharmacophore, i.e., within the confines of the "D-n-QZ" chemical architecture, active compounds may be defined with enhanced antimalarial properties, antiparasitic properties, diminished toxicity, improved bioavailability, and improved efficacy in treatment and prevention of a broader range of infectious agents of humans, animals, and plants.

TABLE 4

Superior anti-malarial potency of omega-trifluoromethyl-alkyl and alkoxy derivatives of aromatic ketones such as: naphthoquinones, xanthones, and anthrones.

| # | Compound | D6 $IC_{50}$, nM |
|---|---|---|
| 47 | 2-hydroxy-1,4-naphthoquinone | 1,800 |
| 48 | 2-(5,5,5-trifluoropentyloxy)-1,4-naphthoquinone | 51.1 |
| 49 | 2-(6,6,6-trifluorohexyl)-1,4-naphthoquinone | 822.7 |
| 50 | 2-(5,6,6,6-tetrafluoro-4,4,4-trifluoromethyl-hexyloxy)-1,4-naphthoquinone | 10.5 |
| 51 | 2-(5,6,6,6-tetrafluoro-4,4,4-trifluoromethyl-hexyloxy)-3-hydroxy-1,4-naphthoquinone | 1.2 |
| 52 | 3,6-dihydroxyxanthone | >100,000 |
| 53 | 3-(6,6,6-trifluorohexyloxy)-6-hydroxyxanthone | 780 |
| 54 | 2-hydroxy-9-anthrone | 8,300 |
| 55 | 2-(6,6,6-trifluorohexyloxy)-9-anthrone | 510 |

*Data are the average of at least 3 independent experiments, each performed in triplicate with the aid of a Precision 2000 robotic pipeting station. $IC_{50}$ values were determined by the MSF assay described by Smilkstein et al., Antimicrob Agents Chemother 48:1803-6, 2004. Results did not vary by more than 15% between experiments.

Example 8

Veterinary Applications

The present example identifies the utility of the present inventive compositions for use in veterinary applications, such as in the preparation of veterinary medicaments for inhibiting, controlling and/or immunizing an animal against insect borne and/or transmitted diseases. Some of these diseases include, by way of example and not limitation, coccidiosis. By way of specific example, the compositions may be included as an active ingredient in the formulation of a treatment for commercially important animals, such as chickens, in preventing and/or treating such parasite-borne diseases, including coccidiosis.

The parasitic diseases may be further described as human parasitic diseases. By way of example, such human or animal parasitic diseases include malaria, toxoplasmosis, amebiasis, giardiasis, leishmaniasis, trypanosomiasis, coccidiosis, caused by organisms such as *Toxoplamosa*, *Eimeria* sp., *Babesia bovis*, *Theileria* sp., and also includes infections by helminths, such as *ascaris*, schistosomes and filarial worms. The present compositions and methods are also effective in the treatment of fungal pathogens including *Pneumocystis carinii*, *Aspergillus fumigatus*, and others.

In particular aspects, the parasitic diseases may be caused by parasites that cause malaria. Particular species of parasites that are included within this group include all species that are capable of causing human infection. By way of example and not exclusion, such species of parasites include *Plasmodium falciparum, Plasmodium vivax, Plasmodium ovale*, and *Plasmodium malariae*.

In other embodiments, the invention provides for a treatment regimen comprising administering to an animal in need thereof an effective amount of a pharmaceutically acceptable preparation of the compound of Formula I, alone or in combination with another pharmaceutically active component. In some embodiments, a combination of the compound of Formula I may be administered as part of a treatment regimen with quinine, quinones, chloroquine, atovaquone, proguanil, clopidol, pyridone/pyridinol analogs (e.g., clopidol), primaquine, amodiaquine, mefloquine, artemisinin, methylene blue, 7-chloro-10-hydroxy-3-(4-trifluoromethylphenyl)-3,4-dihydroacridine-1,9 (2H,10H)-dione (Floxacrine®), pyrimethamine sulfadoxine, artemether-lumefantrine (Coartem®), dapsone-chlorproguanil (LAPDAP®), artesunate, quinidine, dihydroartemisinin, atovaquone, Malarone® (mixture of atovaquone and proguanil) or any combination of these.

In yet another aspect, the herein described compounds are formulated into pharmaceutical compositions for administering to subjects in a biologically compatible form suitable for administration in vivo.

In yet other aspects, the invention provides methods for the treatment of fungal infections. By way of example, these fungal infections are human or animal fungal infections, such as *pneumocystis*

Example 9

Agricultural Applications and Compositions

The present example identifies the utility of the present inventive compositions for use as crop protection agents, particularly in agricultural applications, such as in the preparation of pesticides and products containing pesticides, for use in controlling crop loss associated with plant pathogens that are transmitted by parasites, such as *Phytophthera infestans, Diabrotica balteata, Monilinia fructicola, Nilaparvata lugens*, (*Uncinula necator, Bemisia tabaci Tetranychus urticae*, (*Aonidiella aurantii*, and *Botrytis cinerea*) and *Panonychus ulmi*.

The present example also demonstrates the utility of the present compositions as active agents for use in the treatment and/or prevention of plant fungal infections, such as those that currently compromise various agricultural industries. In particular, the fluoro-alkyl/alkoxy aromatic compounds possess an antifungal activity that may be used to control a number of common plant pathogens that reduce crop yields.

The present example identifies the utility of the present inventive compositions for use in the agricultural industry, specifically as part of a preparation for reducing, controlling and/or eliminating insect-transmitted diseases in commercially significant crops, such as in the apple industry, grape industry, and others.

The crop protection agents of the invention are also suitable for protecting vegetative reproduction material, e.g. seeds, such as fruits, tubers, grains, or plant seedlings, from animal pests. The reproductive material may be treated with the composition before the start of cultivation, seeds, for example, being dressed before they are sown. The active ingredients of the invention can also be applied to seeds (coating) by either soaking the seeds in a liquid preparation of the active ingredient(s), or coating with a solid, such as a powder, or semi-solid, such as a gel, preparation of the active ingredient(s).

The composition can also be given when the reproductive material is introduced to the place of cultivation, e.g., when the seeds are sown in a seed furrow. The treatment procedures for vegetative reproductive material thus treated are further objects of the invention.

Some of the plants and agricultural crops susceptible to plant pathogens and plant diseases that may be treated with the herein described alkyl/alkoxy aromatic compounds include several important food crops. Some of these important food crops include wheat (wheat rust, rye ergot), peanuts (aflatoxin), potatoes (*Phytophthera infestans*, potato lateblight), corn (*Diabrotica balteata*), peaches (*Monilinia fructicola*, brown rot), rice (*Nilaparvata lugens*), grapes (*Uncinula necator*, grapevine powdery mildew), beans (*Bemisia tabaci* and *Tetranychus urticae*) and plants of the genus *Solanum*, including potatoes (*Aonidiella aurantii*) and tomatoes (late blight fungus), and strawberries (*Botrytis cinerea*, grey mold).

The present compositions may also be included in the management of orchard crop yields, such as apple orchards (*Panonychus ulmi*), to protect the crops from major fungal diseases such as scab, powdery mildew, and rust.

The invention in yet another aspect provides a method of enhancing agricultural crop yield and for treating plant pathogens and preventing or inhibiting plant pathogen spread and infectivity. The alkyl/alkoxy aromatic compounds may be used either alone or in combination with other plant pest management treatments. By way of example, other fungicides that may be used in combination preparation with the presently disclosed compounds include sulfur-based preparations (wettable sulfur), sterol inhibitors and strobilurins, as well as a "Bordeaux mixture" (combination of copper sulfate and lime, used to treat late blight fungus).

By way of example, the fluoro-alkyl/alkoxy aromatic compounds may be formulated alone or in combination with another active component such as a pyridone derivative (e.g., clopidol or a structural analog of clopidol) to provide a treatment for application to a plant and/or agricultural crop of interest. Assessment of the relative pesticidal activity of any of the herein described compounds is identified by preparing a spray mixture containing the active ingredient at a concentration of between about 100 ppm to about 400 ppm, and applying the spray mixture to the particular plant of interest.

Potatoes:

For example, with regard to potatoes, any one of the compounds enumerated in Table 1 may be prepared as an aqueous emulsion mixture containing, for example, 400 ppm of one of the active ingredients of Table 1. The potato tubers would first be colonized with crawlers of *Aonidiella aurantii*. After about 2 weeks, the potatoes will be immersed in the aqueous emulsion or a suspension spray mixture containing the 400 ppm of active ingredient. After the tubers have dried off, they may be incubated in a plastic container. Evaluation may take place 10 to 12 weeks later by comparing the survival rate of the crawlers of the first secondary generation of the treated population with that of untreated control batches. The efficacy of the particular agent is thereby assesed relative to improving potatoe yield.

Apples:

In another example, the various active agents of Table 1 may be assesed relative to use in the management of apple yields. A significant problem associated with yield loss associated with apple orchards is *Panonychus ulmi*. In order to provide an effective pesticide according to the present invention for the control of this particular agricultural product, an aqueous emulsion spray mixture containing 400 ppm of the active ingredient may be prepared, and sprayed onto a sample of apple seedlings that have previously been colonized with adult females of *Panonychus ulmi* for about 7 days. These infected plants will be sprayed with the aqueous emulsion spray until they are dripping wet, after which time they will be cultivated in a greenhouse. After 14 days, they may be evaluated. This evaluation will be made by assessing the percentage reduction of the population (% response) as determined by comparing the number of dead spider mites on the treated plants with those on the untreated plants.

Example 10

Oxygen Consumption Inhibition and Synergistic Compound Combinations

The present example demonstrates the utility of the present compounds for blocking oxygen consumption by parasites. By way of example, the compound atovaquone is known to block oxygen consumption by parasites. While not intending to be limited to any mechanism of action, it is contemplated that some of the presently described compounds may act through inhibiting parasite growth through inhibition of the enzyme cytochrome b.

As shown in FIG. 3, the ability of 2-methyl-3-(6,6,6-trifluorohexyl)-7-methoxy-4-quinolone is shown to block respiration (oxygen consumption) by *Plasmodium* infected red blood cells to a degree that is equivalent to atovaquone at equimolar concentrations while NAP 005 (2-(5,6,6,6-tetrafluoro-5-trifluoromethyl-hexyloxy)[1,4]naphthoquinone) does not. Both of these claimed compounds exhibit $IC_{50}$ values in the low nanomolar range against multidrug resistant *Plasmodium falciparum* parasites The present example also demonstrates the utility of the present invention for providing synergistic combinations of the various anti-malarial preparations described herein. By way of example, such as preparation is described herein that includes a pyridine or pyridinol, such as clopidol.

For example, as shown in FIG. 4, an isobolar analysis is presented of the combination of 2-methyl-3-(6,6,6-trifluorohexyl)-7-methoxy-4(1H)-quinolone and clopidol in vitro. Values below the theoretical straight line of addition are considered to be indicative of synergism. This study was performed with the multidrug resistant Dd2 strain of *P. falciparum.*

BIBLIOGRAPHY

The references listed below as well as all references cited in the specification are incorporated herein by reference to the extent that they supplement, explain, provide a background for or teach a methodology, techniques, and/or compositions employed herein.

Ambroise-Thomas, P. (1997), *Bull. Acad. Natl. Med.,* 181:1637-50.

Atkinson, C. T., and M. Aikawa (1990), *Blood Cells,* 16:351-68.

Ballou, W. (1995), Editorial: "Making readiness a priority in the diagnosis and treatment of malaria". *Federal Practitioner.*

Bojang, K. A., et al. (1997), *Parasite Immunol.*, 19:579-81.
Boudreau, E., et al. (1993), *Trop. Med. Parasitol*, 44:257-65.
Brewer, T. G., et al. (1998), *Med. Trop. (Mars)*, 58:22-7.
Brewer, T. G., et al. (1994), *Trans. R. Soc. Trop. Med. Hyg.*, 88 (Suppl. 1):S33-6.
Broudy, V. C., et al. (1986), *Blood*, 68:530-4.
Clark, R. L., et al. (2004), *Birth Defects Res. B Dev. Reprod. Toxicol.*, 71:380-394.
Coleman, R. E., et al. (1992), *Am. J. Trop. Med. Hyg.*, 46:169-82.
Croft, S. L., et al. (1992), *J. Antimicrob. Chemother*, 30:827-32.
Doolan, D. L., et al. (1998), *Curr. Top. Microbial. Immunol.*, 226:37-56.
Fivelman, Q. L., et al. (2004), *Antimicrob. Agents Chemother.*, 48:4097-102.
Fusetti, M., et al. (1999), *Clin. Ter.*, 150:379-82.
Guillouzo, A. (1998), *Environ. Health Perspect.*, 106 (Suppl 2):511-32.
Hudson, A. T. (1993), *Parasitol Today*, 9:66-8.
Hudson, A. T., et al. (1991), *Drugs Exp. Clin. Res.*, 17:427-35.
Ignatushchenko, M. V., et al. (1997), *FEBS Lett.*, 409:67-73.
Ignatushchenko, M. V., et al. (2000), *Am. J. Trop. Med. Hyg.*, 62:77-81.
Kelly, J., et al. (2001), *J. Inorg. Biochem.*, 86:617-25.
Kelly, J. X., et al. (2002), *Antimicrob. Agents Chemother.*, 46:144-50.
Kelly, J. X., et al. (2002), *Mol. Biochem. Parasitol.*, 123:47-54.
Kessl, J. J., et al. (2005), *J. Biol. Chem.*, 280 (17): 17142-8
Kessl, J. J., et al. (2004), *J. Biol. Chem.*, 279:2817-24.
Korsinczky, M., et al. (2000), *Antimicrob. Agents Chemother.*, 44:2100-8.
Krungkrai, J. (2004), *Parasitology*, 129:511-24.
Learngaramkul, P., et al. (1999), *Mol. Cell Biol. Res. Commun.*, 2:15-20.
Li, A. P., et al. (1999), *Chem. Biol. Interact.*, 121:17-35.
Low, L. K. (1998), Chapter #3. "Metabolic changes of drugs and related organic compounds", p. 43-122. In J. N. Delgado and W. A. Remers (ed.), *Wilson and Gisvold's Textbook of Organic Medicinal and Pharmaceutical Chemistry*, 10th ed. Lippincott—Raven Publishers, Philadelphia.
Luzzi, G. A., and T. E. Peto. (1993), *Drug Saf*, 8:295-311.
Madan, A., et al. (1999), *Drug Metab. Dispos.*, 27:327-35.
Makler, M. T., et al. (1991), *Am. J. Trop. Med. Hyg.*, 44:11-6.
Meshnick, S. R., and B. Trumpower (2005), *J. Infect. Dis.*, 191:822.
Milhous, W. K. (2001), *Med. Trop. (Mars)*, 61:48-50.
Olliaro, P. L., and Y. Yuthavong (1999), *Pharmacol. Ther.*, 81:91-110.
Pessina, A., et al. (2003), *Toxicol. Sci.*, 75:355-67.
Pessina, A., et al. (2002), *Altern. Lab Anim.* 30 (Suppl. 2):75-9.
Raether, W., and E. Fink (1979), *Ann. Trop. Med. Parasitol.*, 73:505-26.
Raether, W., and H. Mehlhorn (1984), *Zentralbl. Bakteriol. Mikrobiol. Hyg.* [A], 256:335-41.
Rathbun, R. K., et al. (2000), *Blood*, 96:4204-11.
Schmidt, L. (1979), *Antimicrobial Agents and Chemotherapy*, 16:475-485.
Singh, N., and S. K. Puri (2000), *Acta. Trop.*, 77:185-93.
Slomianny, C., and G. Prensier (1990), *J. Protozool*, 37:465-70.
Smilkstein, M., et al. (2004), *Antimicrob. Agents. Chemother.*, 48:1803-6.
Srivastava, I. K., et al. (1999), *Mol. Microbiol.*, 33:704-11.
Srivastava, I. K., et al. (1997), *J. Biol. Chem.*, 272:3961-6.
Suswam, E., D. Kyle, and N. Lang-Unnasch (2001), *Exp. Parasitol.*, 98:180-7.
Taylor, W. R., and N. J. White (2004), *Drug Saf.*, 27:25-61.
Toovey, S., and A. Jamieson (2004), *Trans. R. Soc. Trop. Med. Hyg.*, 98:261-9.
Trouiller, P., and P. L. Olliaro (1998), *Int. J. Infect. Dis.*, 3:61-3.
Trouiller, P., and P. L. Olliaro (1999), *Lancet*, 354:164.
Turker, M. S. (1998), *Semin. Cancer Biol.*, 8:407-19.
Vaidya, A. (1998), "Mitochondrial physiology as a target for atovaquone and other anti-malarials.", p. 355-368. In: I. Sherman (ed.), Malaria: parasite biology, pathogenesis, and protection. *American Society for Microbiology*, Washington D.C.
Vaidya, A. B., and M. W. Mather (2000), *Drug Resist. Updat.*, 3:283-287.
Varney, N. R., D. Campbell, and R. J. Roberts (1994), *Arch. Clin. Neuropsychol.*, 9:347-52.
Varney, N. R., et al. (1997), *J. Nerv. Ment. Dis.*, 185:695-703.
Via, L. E., et al. (1998), *J. Cell. Sci.*, 111:897-905.
Weina, P. J. (1998), *Mil. Med.*, 163:635-9.
Winkelmann, E., and W. Raether. (1987), *Arzneimittelforschung*, 37:647-61.
U.S. Pat. No. 4,250,182—Govin (1981).
U.S. Pat. No. 5,977,077—Winter et al. (1999).
U.S. Pat. No. 6,248,891—Sharp et al. (2001).
U.S. Pat. No. 6,541,483—Michejda et al. (2003).
U.S. Pat. No. 6,631,797—Winter et al. (2003).
U.S. Pat. No. 6,703,388—Mijamoto et al. (2004).
U.S. Pat. No. 3,981,903—Hirano et al. (1976)
U.S. Pat. No. 6,686,469—Eberle et al. (2004)
U.S. Published Patent Application No. 2002/0055644A1—Winter et al. (2002).
Peters, W., et al. (1975), *Ann. Trop. Med. Parasitol.*, 69: 311-28.
Ager et al. (1984). *Rodent malaria models*, 68/I. Springer-Verlag, Berlin.
Adams, P. A., et al. (1996), J. Inorg. Biochem., 63:69-77.
Ahua, K. M., et al. (2004), Phytochemistry, 65:963-8.
Bastow, K. F. (2004), Curr. Drug Targets Infect. Disord., 4:323-30.
Carter, R., and K. N. Mendis. (2002), Clin. Microbiol. Rev., 15:564-94.
Fujioka, H., et al. (1990), Arzneimittelforschung, 40:1026-9.
Lowden, C. T., and K. F. Bastow. (2003), Antiviral Res., 59:143-54.
Luzzi, G. A., and T. E. Peto. (1993), Drug Saf., 8:295-311.
Michael, J. P. (2001), Nat. Prod. Rep., 18:543-59.
Michael, J. P. (2003), Nat. Prod. Rep. 20:476-93.
Phillips-Howard, P. A., and F. O. ter Kuile (1995), Drug Saf., 12:370-83.
Sachs, J., and P. Malaney (2002), Nature, 415:680-5.
White, N. J. (2004), J. Clin. Invest., 113:1084-92.
White, N. J., et al. (1999), Lancet, 353:1965-7.
Remington: The Science and Practice of Pharmacy, 21st Edition, 2005, the Philadelphia College of Pharmacy and Science.
Oettmeier, W. (1994), Biochim. Biophys. Acta, 1188, 125-130.
Gogal et al. (1994), J. Immunol. Methods, 170 (2): 211-224.
Fidock et al. (2004), Nat. Rev. Drug Discov., 3: 509-20.

What is claimed is:

1. A composition having as an active agent a compound having a structure:

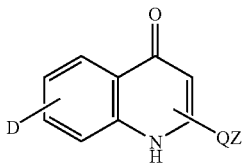

wherein:
Q is a —O— or —CH$_2$— moiety;
Z is a moiety comprising a linear or branched chain alkyl or alkene moiety terminated by one or more fluorine atoms; and
D is an alkyl, alkoxy, carboxy or amino moiety, wherein there may be one or more D moieties, which may be the same or different, located at more than one location
wherein said composition has an anti-parasitic activity for preventing, reducing or inhibiting growth of a microorganism.

2. The composition of claim 1, wherein Z is a moiety terminated by a group —CH$_2$F, —CHF$_2$, —CF$_3$, —C$_2$F$_5$, n-C$_3$F$_7$, i-C$_3$F$_7$, n-C$_4$F$_9$, i-C$_4$F$_9$, or —SF$_5$.

3. The composition of claim 1, wherein QZ is a moiety comprising a 6,6,6-trifluoro-hexyloxy group.

4. The composition of claim 1, wherein the active agent is 3-carboxymethyl-7-(6,6,6-trifluoro-hexyloxy)-4-(1H)-quinolone.

5. The composition of claim 1, wherein the active agent is a structural analog of 3-carboxy-7-(6,6,6-trifluoro-hexyloxy)-4(1H)-quinolone.

6. A composition comprising as an active agent a fluoroalkyl/alkoxy aromatic compound having a structure of Formula I, D-n-QZ wherein n is a moiety comprising a 4(1H)-quinolone aromatic ring system having a structure:

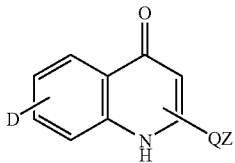

wherein D is an alkyl, alkoxy, carboxy or amino moiety located at 1 or more positions of the aromatic ring system not otherwise occupied by QZ;
Q is a moiety comprising a methylene (CH$_2$) group located at a position of the aromatic ring system not otherwise occupied by D; and
Z is a moiety comprising a six (6) carbon alkyl chain that includes 1 or more terminal fluorine (F) substitutions.

7. The composition of claim 6 wherein Z is a moiety comprising a six (6) carbon alkyl having a tri-fluorine substituted terminal carbon moiety.

8. The composition of claim 7 wherein the active agent is 2-methyl-3-(6,6,6-trifluoro-hexyl)-7-methoxy-4-(1H)-quinolone, having an IC$_{50}$ of about 10 nM against a drug-sensitive strain (D6), and against a multi-drug resistant strain (W2), of Plasmodium falciparum, and having an IC$_{50}$ of >2,500 nM against concanavalin A-induced murine splenic lymphocyte proliferation.

9. A composition comprising as an active agent a fluoroalkyl/alkoxy aromatic compound having a structure of Formula I, D-n-QZ wherein n is a moiety comprising a quinolone aromatic ring system having a structure:

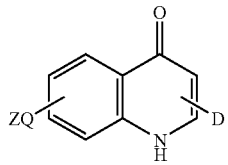

and wherein 1 or more of the positions of the aromatic system not otherwise occupied by QZ is D which is an alkyl, alkoxy, carboxy or amino moiety;
Q is —O— moiety; and
Z is a moiety comprising a 6-carbon alkyl terminated by 1 or more fluorine atoms.

10. The composition of claim 9 wherein the active agent is 7-(6,6,6-trifluorohexyloxy)-3-carboxylic acid ethyl ester and has an IC$_{50}$ value of about 1 nM against a drug sensitive (D6) strain of Plasmodium falciparum and against multi-drug resistant Plasmodium falciparum strain W2, strain Dd2, Strain 7G8 or strain Tm93C1088.

11. An antiparasitic agent comprising a composition as defined in claim 1, physiologically acceptable addition compounds thereof, or E/Z isomers or tautomers thereof.

12. An antiparasitic agent comprising a clopidol or a structurally related pyridinol or pyridine analog, and the composition of claim 1.

13. An antiparasitic agent comprising an antimalarial drug comprising quinine, chloroquine, dapsone, amodiaquine, atovaquone, or an endoperoxide, and the composition of claim 1.

14. The antiparasitic agent of claim 13 wherein the endoperoxide is artemisinin.

15. An agrochemically acceptable pesticidal preparation comprising a composition as defined in claim 1, physiologically acceptable addition compounds thereof, or E/Z isomers or tautomers thereof.

16. The composition of claim 1, wherein the Z moiety comprises a linear or branched chain alkyl or alkene moiety of 4 to 14 carbons in length terminated by one or more fluorine atoms.

17. The composition of claim 1, wherein there are more than one D moieties.

18. The composition of claim 17, wherein the more than one D moieties are each different.

19. A method for treating a parasitic disease in a subject, comprising administering to the subject an effective amount of the composition of claim 1.

* * * * *